(12) United States Patent
Nozoe et al.

(10) Patent No.: US 9,822,237 B2
(45) Date of Patent: Nov. 21, 2017

(54) RESIN COMPOSITION, FILM, POLARIZING PLATE PROTECTIVE FILM, POLARIZING PLATE, LIQUID CRYSTAL DISPLAY DEVICE, AND BIS TYPE ALICYCLIC CARDO PHENOL COMPOUND

(71) Applicant: FUJIFILM Corporation, Tokyo (JP)

(72) Inventors: Yutaka Nozoe, Kanagawa-ken (JP);
Shusuke Arita, Kanagawa-ken (JP);
Jun Nakabayashi, Kanagawa-ken (JP)

(73) Assignee: FUJIFILM CORPORATION, Tokyo (JP)

( * ) Notice: Subject to any disclaimer, the term of this patent is extended or adjusted under 35 U.S.C. 154(b) by 65 days.

(21) Appl. No.: 14/867,441

(22) Filed: Sep. 28, 2015

(65) Prior Publication Data
US 2016/0090467 A1    Mar. 31, 2016

(30) Foreign Application Priority Data
Sep. 29, 2014    (JP) .................................. 2014-198674

(51) Int. Cl.
*C09K 19/00* (2006.01)
*C08K 5/13* (2006.01)
(Continued)

(52) U.S. Cl.
CPC ................ *C08K 5/13* (2013.01); *C07C 39/17* (2013.01); *G02B 1/14* (2015.01);
(Continued)

(58) Field of Classification Search
CPC ..... C08K 5/13; G02F 1/133528; C07C 39/17;
C07C 43/196; C07C 2101/08; C07C 2101/14; G02B 1/14; H01L 21/0273; H01L 21/0271; Y10T 428/10; Y10T 428/1059; Y10T 428/1077; Y10T 428/1086
USPC ..... 428/1.1, 1.5, 1.54, 1.6; 349/96; 568/660, 568/720; 359/507; 106/287.26, 170.52; 524/326

See application file for complete search history.

(56) References Cited

U.S. PATENT DOCUMENTS

2010/0292368 A1* 11/2010 Takebe .................. C08J 5/18
                                                524/37
2014/0235057 A1*  8/2014 Hatakeyama ............ G03F 7/00
                                                438/702
2016/0053062 A1*  2/2016 Maeda .................... C08L 33/12
                                                428/220

FOREIGN PATENT DOCUMENTS

JP          S49-250 A       1/1974
JP          H05-297583 A   11/1993
(Continued)

OTHER PUBLICATIONS

Notification of Reasons for Refusal issued by the Japanese Patent Office dated Oct. 25, 2016, in connection with related Japanese Patent Application No. 2014-198674.

*Primary Examiner* — Ruiyun Zhang
(74) *Attorney, Agent, or Firm* — Edwards Neils LLC; Jean C. Edwards, Esq.

(57) ABSTRACT

A resin of the present disclosure includes a resin and a compound represented by General Formula I below.

(Continued)

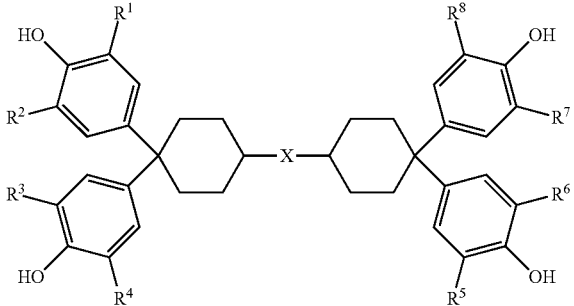

[General Formula I]

wherein each of $R^1$, $R^2$, $R^3$, $R^4$, $R^5$, $R^6$, $R^7$ and $R^8$ represents a hydrogen atom, a halogen atom, a hydroxyl group, or an aliphatic hydrocarbon group having a carbon number within a range from 1 to 8, and X represents a divalent linking group constituted by at least one species selected from among a single bond, an ether bond, and an alkylene group having a carbon number within a range from 1 to 15.

12 Claims, 3 Drawing Sheets

(51) Int. Cl.
  *C07C 39/17* (2006.01)
  *G02B 1/14* (2015.01)
  *G02F 1/1335* (2006.01)
(52) U.S. Cl.
  CPC .... *G02F 1/133528* (2013.01); *C07C 2601/08* (2017.05); *C07C 2601/14* (2017.05); *Y10T 428/10* (2015.01); *Y10T 428/1059* (2015.01); *Y10T 428/1077* (2015.01)

(56) References Cited

FOREIGN PATENT DOCUMENTS

| JP | H06-116364 A | 4/1994 |
| JP | 2000-034248 A | 2/2000 |
| JP | 2007-199606 A | 8/2007 |
| JP | 2008-230984 A | 10/2008 |
| JP | 4410540 B2 | 2/2010 |
| JP | 2011-144344 A | 7/2011 |
| JP | 2011148713 A * | 8/2011 |
| JP | 2012-185291 A | 9/2012 |

* cited by examiner

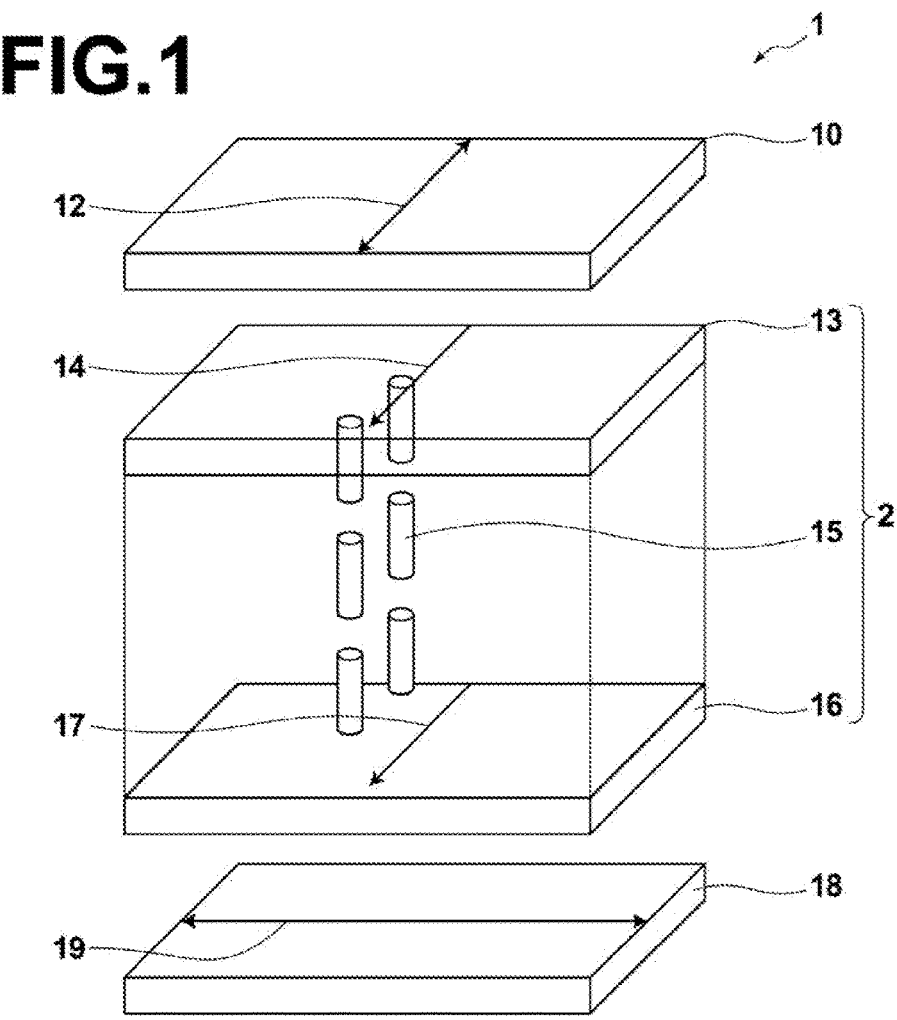
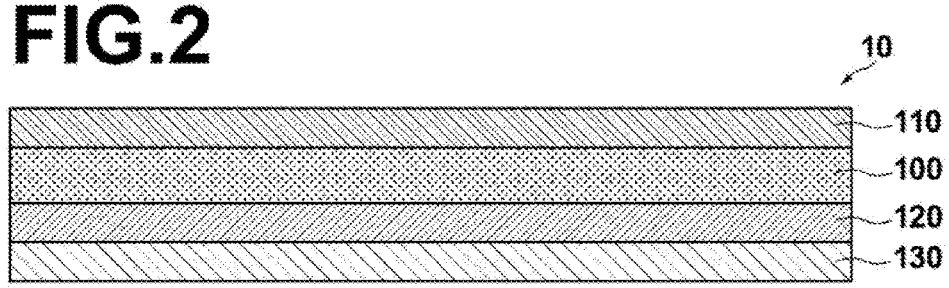

RESIN COMPOSITION, FILM, POLARIZING PLATE PROTECTIVE FILM, POLARIZING PLATE, LIQUID CRYSTAL DISPLAY DEVICE, AND BIS TYPE ALICYCLIC CARDO PHENOL COMPOUND

CROSS REFERENCE TO RELATED APPLICATIONS

The present application claims priority under 35 U.S.C. §119 to Japanese Patent Application No. 2014-198674 filed on Sep. 29, 2014. The above application is hereby expressly incorporated by reference, in its entirety, into the present application.

BACKGROUND

The present disclosure is related to a film which is favorably suited for use as an optical film such as a polarizing plate protective film, a bis type alicyclic cardo phenolic compound and a resin composition that provides the film, a polarizing plate protective film equipped with the film, a polarizing plate, and a liquid crystal display device.

Demand is growing for liquid crystal display devices, in applications such as liquid crystal displays for LCD TVs and personal computers. Generally, a liquid crystal display device includes a liquid crystal panel member having a polarizing plate on both sides of liquid crystal cells, and display is performed by controlling light emitted from a backlight member with the liquid crystal panel member. The polarizing plate is configured with a polarizer and at least one polarizing plate protecting film.

Due to recent advances in technology, the sizes of liquid crystal display devices are increasing at an accelerated pace, and the applications of LCD's are being diversified. Use of LCD's in various environments is being considered, and there is demand for solutions to problems associated with use in various environments. For example, when using liquid crystal displays outdoors, degradation due to moisture absorption of polarizers is a problem. Therefore, low moisture permeability is an important issue in polarizing plate protective films that cover the surfaces of polarizers.

Films formed from acrylic resins (acrylic resin films) such as polymethyl methacrylate (PMMA) are known as low moisture permeability films. However, the moisture permeability of the acrylic resin films are not sufficient for polarizing plate protective films assuming outdoor use, and further low moisture permeability is required.

Meanwhile, mixing a low molecular weight substance as an additive to resin is a method for imparting a function to the resin. For example, Japanese Patent No. 4410540 and Japanese Unexamined Patent Publication No. 2011-144344 disclose increasing the refractive index of a resin composition or plasticizing a resin composition by adding 9,9-bis (mono- to tri-hydroxyphenyl) fluorene compound to cellulose acylate or polycarbonate.

SUMMARY

In the mixing of additives into resins, deterioration of transparency due to poor compatibility between the resin and the additive and reduction in heat resistance due to plasticization are problems. In optical applications such as polarizing plate protective films, it is preferable for the haze value, which is an index of transparency of the film, to be as small as possible, and for the glass transition temperature, which is an index of heat resistance (Tg) to be as high as possible. The heat resistance of the film is also important in ease of production, from the viewpoint of long term reliability as an optical element.

The present disclosure has been developed in view of the above circumstances. The present disclosure provides a resin composition comprising a resin and an additive mixed therein, which is capable of forming a film having a small haze value, heat resistance greater than or equal to the heat resistance inherent to the resin, and a lower moisture permeability than the moisture permeability of the resin. The present disclosure also provides a film formed using the resin composition.

The disclosure also provides a film having a small haze value, heat resistance greater than or equal to the heat resistance inherent to the resin, and a lower moisture permeability than the moisture permeability of the resin, as well as a polarizing plate protective film.

The present disclosure further provides a polarizing plate and a liquid crystal display device in which degradation due to moisture absorption is low.

The present disclosure still further provides a novel bis type alicyclic cardo phenol compound which is favorably suited for use as an additive that imparts low moisture permeability to resins without leading to deterioration in the transparency or heat resistance of the resins.

A resin composition of the present disclosure comprises:
a resin; and
a compound represented by General Formula I below.

[General Formula I]

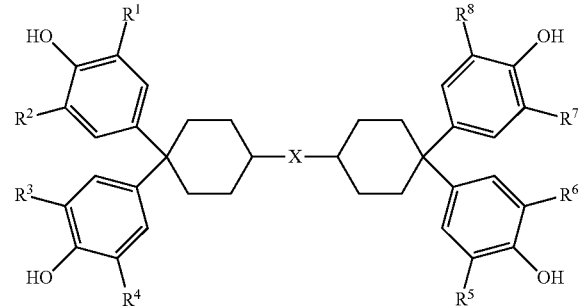

In the formula above, each of $R^1$, $R^2$, $R^3$, $R^4$, $R^5$, $R^6$, $R^7$ and $R^8$ represents a hydrogen atom, a halogen atom, a hydroxyl group, or an aliphatic hydrocarbon group having a carbon number within a range from 1 to 8. X represents a divalent linking group constituted by at least one species selected from among a single bond, an ether bond, and an alkylene group having a carbon number within a range from 1 to 15.

In General Formula I, the aliphatic hydrocarbon groups and the alkylene groups may be any of a straight chain group, a branched group, and a cyclic group.

It is preferable for X to be a divalent linking group constituted by at least one species selected from among an ether bond and an alkylene group having a carbon number within a range from 1 to 10, and more preferably a bivalent linking group which is at least one alkylene group selected from alkylene groups having carbon numbers within a range from 4 to 8. In addition, it is preferable for the number of atoms that bind cyclohexyl groups to each other to be at least 2 or greater in X.

Here, the "the number of atoms that bind cyclohexyl groups to each other to be at least 2 or more in X" means that the alkylene group having the smallest carbon number is an ethylene group in the case that X is an alkylene group. Even if the carbon number itself is 2 or greater, X having an aliphatic hydrocarbon group on the methylene group is not included in this definition.

That X is a single bond means that no atoms exist as X, and the cyclohexyl groups are directly bound to each other.

The numerical ranges expressed by using the term "to" in the present specification refer to ranges including numerical values described before and after "to" as the lower limits and upper limits thereof.

In General Formula I, it is preferable for $R^2$, $R^3$, $R^4$, $R^5$, $R^6$, $R^7$, and $R^8$ to be hydrogen atoms or aliphatic hydrocarbon groups having a carbon number within a range from 1 to 8. Among these, $R^2$, $R^3$, $R^6$, and $R^7$ are more preferably hydrogen atoms, and $R^1$, $R^4$, $R^5$, and $R^8$ are more preferably hydrogen atoms or methyl groups.

Among the bis type alicyclic cardo phenols of General Formula I, bis type alicyclic cardo phenol compounds in which X is a divalent linking group constituted by at least one species selected from among an ether bond and an alkylene group having a carbon number within a range from 1 to 10, and the number of atoms that bind cyclohexyl groups to each other is at least two or greater, as represented by General Formula II below, are novel compounds.

[General Formula I]

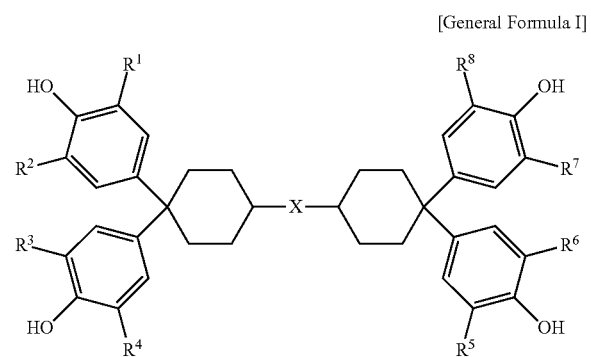

In the formula above, each of $R^1$, $R^2$, $R^3$, $R^4$, $R^5$, $R^6$, $R^7$ and $R^8$ represents a hydrogen atom, a halogen atom, a hydroxyl group, or an aliphatic hydrocarbon group having a carbon number within a range from 1 to 8. X is a divalent linking group constituted by at least one species selected from among an ether bond and an alkylene group having a carbon number within a range from 1 to 10, and the number of atoms that bind cyclohexyl groups to each other is at least two or greater. The aliphatic hydrocarbon groups and the alkylene groups may be any of a straight chain group, a branched group, and a cyclic group.

The resin composition of the present disclosure is favorable in cases that the resin is a cellulose ester resin, an acrylic resin, a polycarbonate resin, or a cycloolefin based resin, and particularly favorably in the case that the resin is an acrylic resin.

In the present specification, the term "acrylic resin" refers to "acrylic resins", "methacrylic resins", "blends of an acrylic resin and a methacrylic resin" and "copolymers of an acrylic monomer and a methacrylic monomer".

In the case that the resin is an acrylic resin, it is preferable for the weight average molecular weight thereof to be from 80,000 to 2,500,000, and more preferably from 250,000 to 2,000,000.

The "weight average molecular weight" as used herein, is the weight average molecular weight measured by gel permeation chromatography (GPC). The details of measurement conditions will be described later.

The acrylic resin includes a unit (a), which is a monomer unit derived from methyl methacrylate, and a unit (b), which is a monomer unit derived from an alkyl(meth)acrylate other than methyl methacrylate. A preferred example is that in which the content of the unit (a) within the total content of the acrylic resin is 95% by mass or greater.

A film of the present disclosure is that which is formed using the resin composition of the present disclosure.

In addition, a polarizing plate protective film of the present disclosure is that equipped with at least one layer of the film of the present disclosure. In addition, the polarizing plate of the present disclosure comprises a polarizer, in which at least one surface of the polarizer is equipped with the polarizing plate protective film of the present disclosure. A liquid crystal display device of the present disclosure comprises a pair of polarizing plates and a liquid crystal cell sandwiched between the pair of polarizing plates, wherein at least one of the pair of polarizing plates is the polarizing plate of the present disclosure.

The resin composition of the present disclosure is a resin, in which the compound represented by General Formula I is mixed in as an additive. According to such a configuration, the resin composition is that capable of forming a film having low haze, which is an index of transparency of the film, heat resistance greater than or equal to the heat resistance inherent to the resin and lower moisture permeability than the moisture permeability inherent to the resin.

The film of the present disclosure is formed using the resin composition of the present disclosure, and the polarizing plate protective film of the present disclosure is equipped with at least one film of the present disclosure. According to such a configuration, the film and the polarizing plate protective film are films having low haze, which is an index of transparency of the film, heat resistance greater than or equal to the heat resistance inherent to the resin and lower moisture permeability than the moisture permeability inherent to the resin.

The polarizing plate and the liquid crystal display device of the present disclosure are equipped with the polarizing plate protective film having low haze, which is an index of transparency of the film, heat resistance greater than or equal to the heat resistance inherent to the resin and lower moisture permeability than the moisture permeability inherent to the resin. According to such a configuration, the polarizing plate and the liquid crystal display device can be those in which deterioration due to moisture absorption is low.

The bis type alicyclic cardo phenolic compound of the present disclosure, is capable of forming a film having low haze, which is an index of transparency of the film, heat resistance greater than or equal to the heat resistance inherent to a resin and lower moisture permeability than the moisture permeability inherent to the resin, by being added to the resin.

BRIEF DESCRIPTION OF THE DRAWINGS

FIG. 1 is a schematic diagram showing the structure of a liquid crystal display device according to one embodiment of the present disclosure.

FIG. 2 is a cross sectional view in the thickness direction showing the configuration of a polarizing plate according to one embodiment of the present disclosure.

DETAILED DESCRIPTION OF THE PREFERRED EMBODIMENTS

Figure 3:
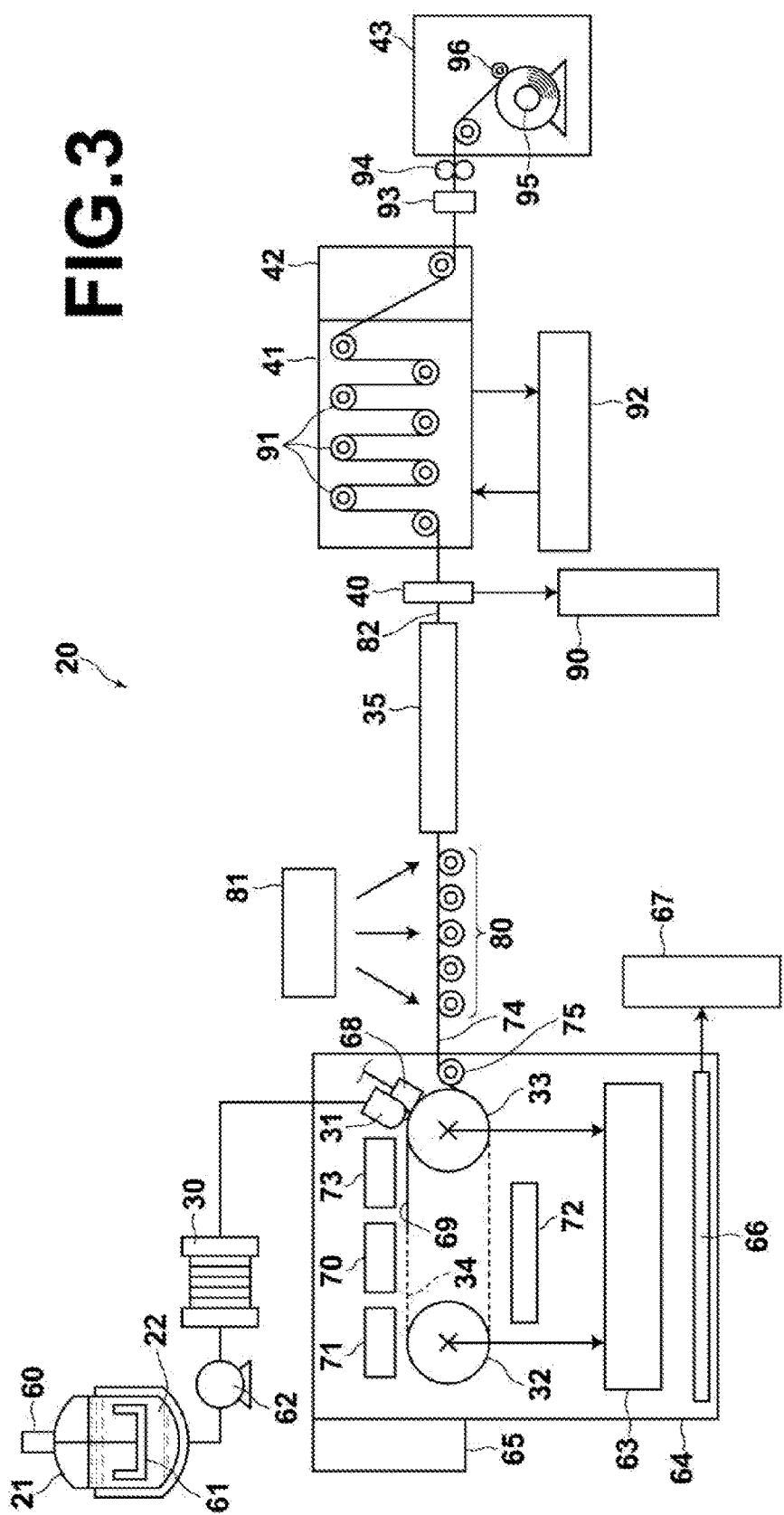
FIG. 3 is a schematic view showing one embodiment of a production line for polarizing plate protective films.

The present disclosure will be described in detail below.

The constituent elements will be described below as exemplary embodiments and specific examples. However, the present disclosure is not limited to such embodiments.
<Resin Composition>

The present inventors considered additive agents to be added to resins for optical applications which are capable of imparting a low moisture permeability to the resins without decreasing the transparency or decreasing the heat resistance thereof, and performed molecular design.

As described in the "SUMMARY" section, generally, the heat resistance of resins deteriorates if low molecular weight compounds are added, due to plasticization. The deterioration of heat resistance due to plasticization is caused by molecular motion of polymer chains constituting resins increasing. The present inventors have attempted to introduce a rigid structure, as a structure that suppresses molecular motion of polymer chains due to interaction with the polymer chains, into a low molecular weight compound capable of imparting a low moisture permeability.

Specifically, phenols were selected as a structure that imparts low moisture permeability, and as a result of molecular design in order to introduce a rigid structure, the bis type alicyclic cardo phenols represented by General Formula I below, was found to be favorably suited as such a rigid structure.

That is, the resin composition of the present disclosure comprises:

a resin; and a compound represented by General Formula I below.

[General Formula I]

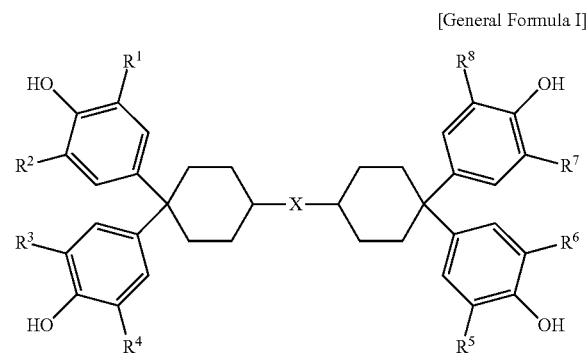

In the formula above, each of $R^1$, $R^2$, $R^3$, $R^4$, $R^5$, $R^6$, $R^7$ and $R^8$ represents a hydrogen atom, a halogen atom, a hydroxyl group, or an aliphatic hydrocarbon group having a carbon number within a range from 1 to 8. X represents a divalent linking group constituted by at least one species selected from among a single bond, an ether bond, and an alkylene group having a carbon number within a range from 1 to 15. Here, the aliphatic hydrocarbon groups and the alkylene groups may be any of a straight chain group, a branched group, and a cyclic group.

<<Bis Type Alicyclic Cardo Phenolic Compound>>

First, the bis type alicyclic cardo phenol compound represented by General Formula I will be described.

The bis type alicyclic cardo phenol compound represented by General Formula I has a specific structure comprising two cycloalicyclic cardo phenols formed by two hydroxyphenyl which are connected via a cyclohexyl group, the two cycloalicyclic cardo phenol being bonded via the linking portion X. The cyclohexyl groups of the cycloalicyclic cardo phenols are bonded to each other via the linking portion X.

Generally, a cardo structure refers to hinge structure in which four aromatic rings are directly bonded to one carbon. Fluorene bisphenols are representative compounds. These compounds are known to be useful as high refractive index materials. In the present disclosure, the left side and the right side of the linking portion X in General Formula I are respectively referred to as alicyclic cardo phenol structure.

In General Formula I, each of $R^1$, $R^2$, $R^3$, $R^4$, $R^5$, $R^6$, $R^7$ and $R^8$ represents a hydrogen atom, a halogen atom, a hydroxyl group, or an aliphatic hydrocarbon group having a carbon number within a range from 1 to 8. It is preferable for the halogen atom to be a fluorine atom, a chlorine atom, a bromine atom, or an iodine atom, and a fluorine atom or a chlorine atom is more preferable. Examples of the aliphatic hydrocarbon group having a carbon number within a range from 1 to 8 include an alkyl group, an alkenyl group, an alkynyl group, and an aryl group. Examples of alkyl groups having a carbon number within a range from 1 to 8 include a straight alkyl group, a branched alkyl group, and a cyclic alkyl group. Specific examples include a methyl group, an ethyl group, an isopropyl group, n-butyl, i-butyl, s-butyl, t-butyl, n-hexyl groups, and a cyclohexyl group.

From the viewpoints of compatibility and moisture permeability, it is preferable for $R^1$, $R^2$, $R^3$, $R^4$, $R^5$, $R^6$, $R^7$ and $R^8$ to be hydrogen atoms or aliphatic hydrocarbon groups having a carbon number within a range from 1 to 8. Among these, $R^2$, $R^3$, $R^6$, and $R^7$ are more preferably hydrogen atoms, and $R^1$, $R^4$, $R^5$, and $R^5$ are more preferably hydrogen atoms or methyl groups, and even more preferably hydrogen atoms.

X is a divalent linking group constituted by at least one species selected from among a single bond, an ether bond and an alkylene group having a carbon number within a range from 1 to 15. It is preferable for X to be a divalent linking group constituted by at least one species selected from among an ether bond and an alkylene group having a carbon number within a range from 1 to 10, and more preferably a divalent linking group composed of an alkylene group having a carbon number within a range from 4 to 8.

Among the bis type alicyclic cardo phenols of General Formula I, bis type alicyclic cardo phenol compounds in which X is a divalent linking group constituted by at least one species selected from among an ether bond and an alkylene group having a carbon number within a range from 1 to 10, and the number of atoms that bind cyclohexyl groups to each other is at least two or greater, as represented by General Formula II below, are novel compounds. In the present disclosure, such compounds are used as additives (resin modifiers) that impart low moisture permeability, but these compounds are also effective as resin modifiers for other applications, or as raw materials for photoresist materials and specialized epoxy materials.

[General Formula II]

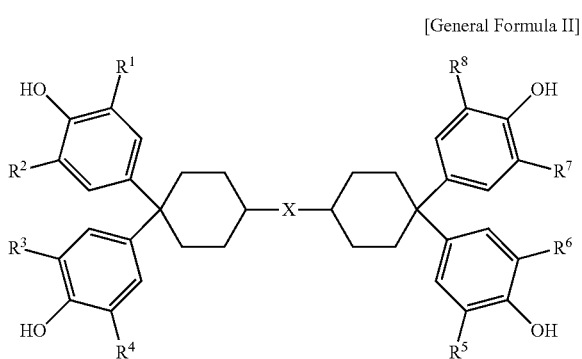

In the formula above, each of $R^1$, $R^2$, $R^3$, $R^4$, $R^5$, $R^6$, $R^7$ and $R^8$ represents a hydrogen atom, a halogen atom, a hydroxyl group, or an aliphatic hydrocarbon group having a carbon number within a range from 1 to 8. X is a divalent linking group constituted by at least one species selected from among an ether bond and an alkylene group having a carbon number within a range from 1 to 10, and the number of atoms that bind cyclohexyl groups to each other is at least two or greater. The aliphatic hydrocarbon groups and the alkylene groups may be any of a straight chain group, a branched group, and a cyclic group.

As shown in the Examples to be described later, the bis type alicyclic cardo phenols represented by General Formula I and General Formula II are additive agents (low molecular weight compounds) that can impart low moisture permeability to resins without causing deterioration in haze and heat resistance when the resins are formed into films.

The bis type alicyclic cardo phenol of General Formula I and General Formula II select a phenol as a structure that imparts low moisture permeability, and molecular design was performed to introduce a rigid structure into the phenol in order to suppress deterioration of heat resistance caused by plasticization due to the addition of the phenol. Meanwhile, it is generally known that there is a trade off relationship between heat resistance and brittleness. The present inventors have found that by adopting a structure having high flexibility as the linking portion X, for example, by designating that the number of atoms that bond the cyclohexyl groups to each other at the linking portion X to be two or greater, an advantageous effect that the deterioration of brittleness can be suppressed is obtained in the bis type alicyclic cardo phenol of General Formula I and General Formula II. Although the mechanism is not clear, it is considered that by having the rigid structure (alicyclic cardo phenol) that interacts with polymer chains to suppress the molecular mobility as well as the flexible connecting portion (X) that anchors them together in a single molecule, both suppression of polymer molecular motion (=imparting heat resistance) and imparting of local motion (=improving brittleness) can be achieved. Also, the bis type alicyclic cardo phenol can be present by being efficiently distributed among the polymer chains, it is possible to highly efficiently impart a low moisture permeability.

An n-ethylene group or an ethylene group with at least one or more alkyl groups is preferable as the linking portion X in which the number of atoms that bond the cyclohexyl groups to each other is 2 or greater. A more preferable example is 1,2-diethyl ethylene groups. Other examples are structures with a methylene group or an ethylene group on one or both sides of an ether bond and the like.

The bis type alicyclic cardo phenol represented by General Formula I of the present disclosure can be obtained by obtaining a hydrogenated phenol derivative by hydrogenation treatment (hydrotreating) of a corresponding phenol derivative, causing it to become a ketone derivative by oxidation, and further by dehydration condensation of a corresponding phenol derivative (see the Examples to be described later). Phenol derivatives which are commercially available as industrial materials may be favorably employed as the phenol derivative which is the starting material. A reaction scheme that shows a simplified synthesizing procedure is shown below.

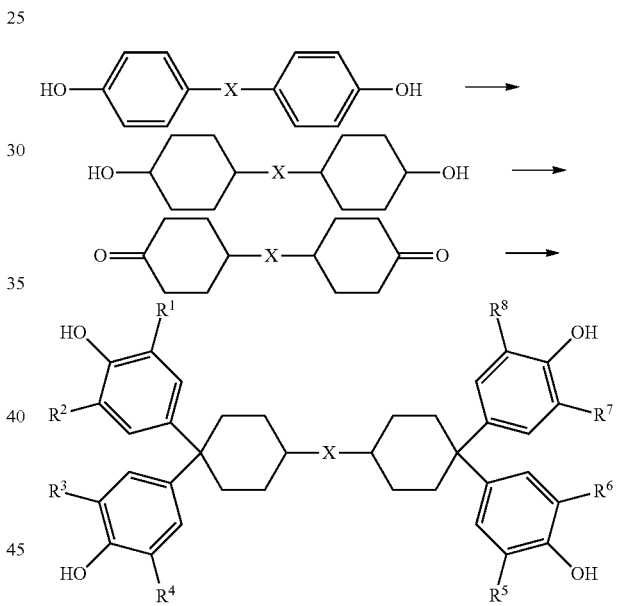

Preferred examples of compounds represented by General Formula I are shown below. However, the present disclosure is not limited to these specific examples.

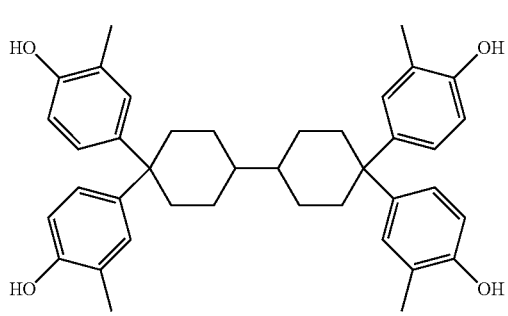

A-1

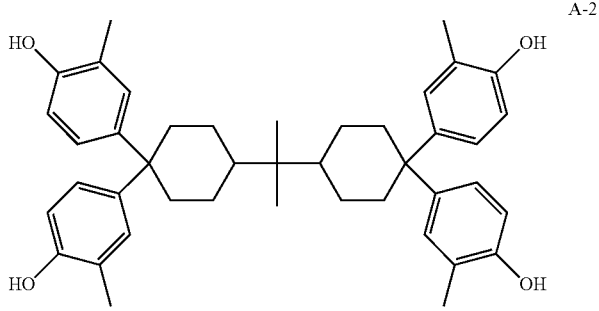

A-2

-continued
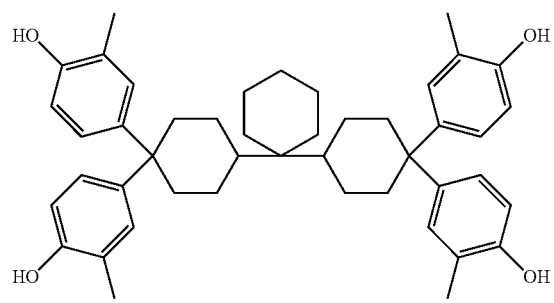
A-3
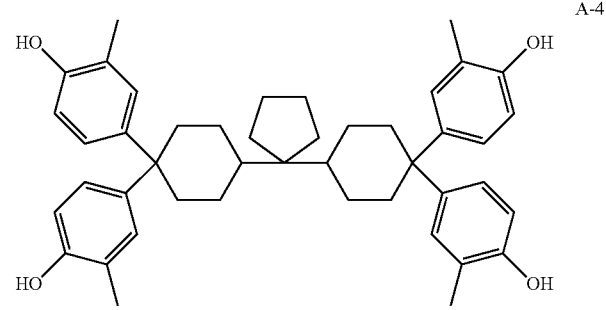
A-4
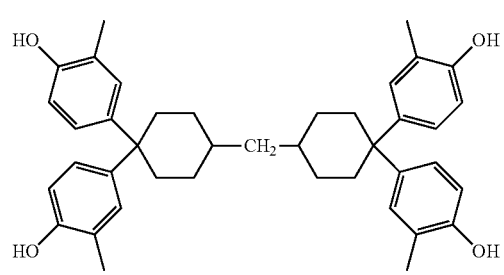
A-5
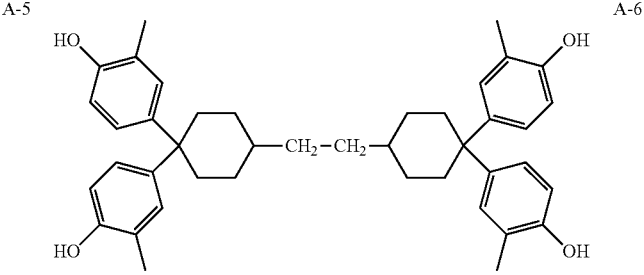
A-6
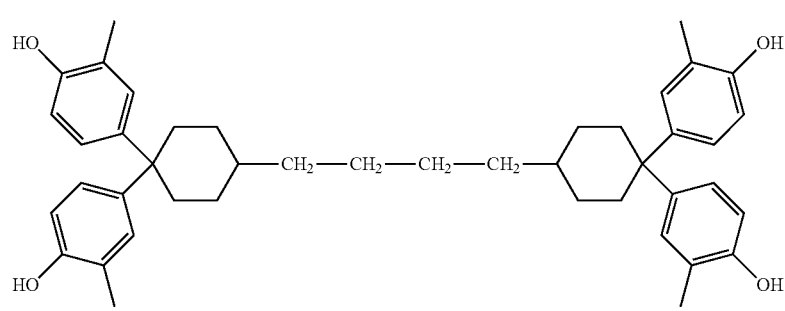
A-7
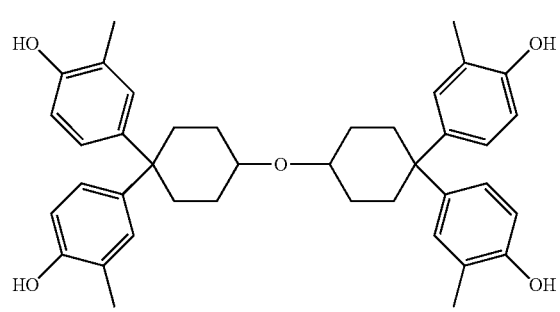
A-8
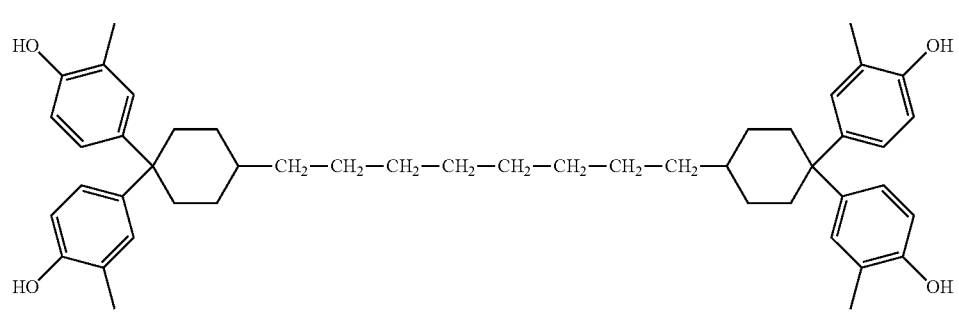
A-9

-continued
A-10
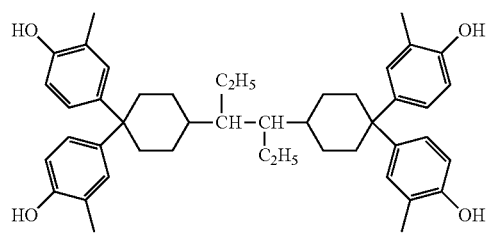
A-11
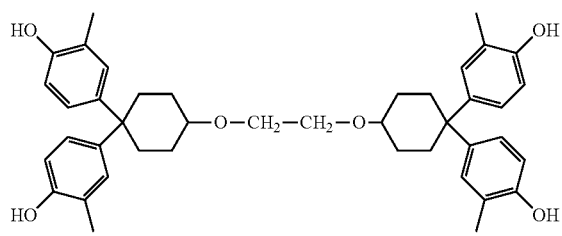
A-12
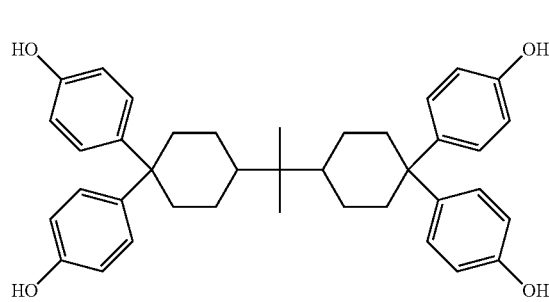
A-13
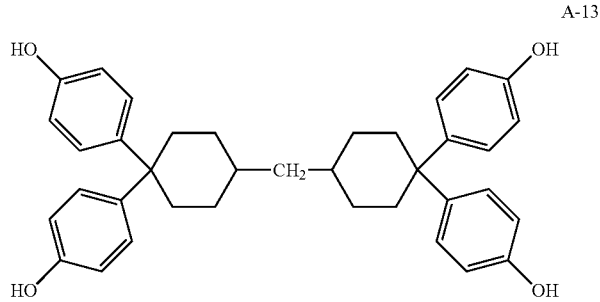
A-14
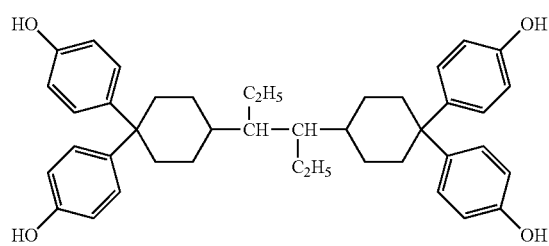
A-15
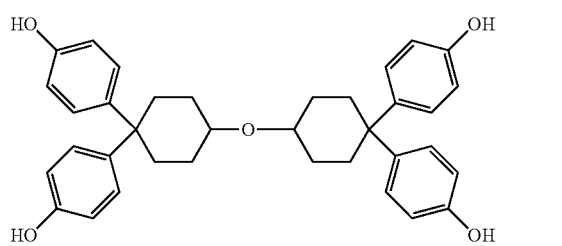
A-16
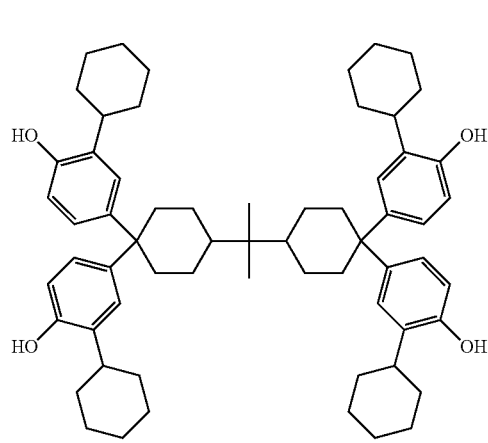
A-17
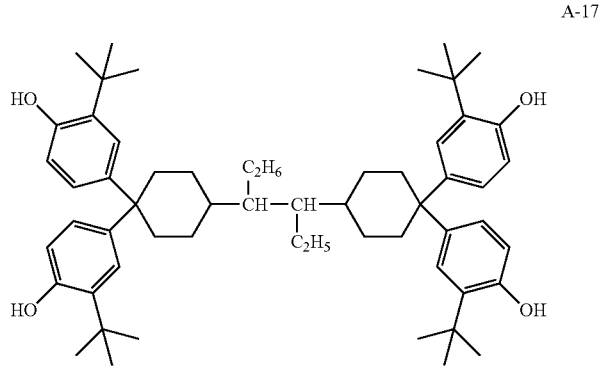
A-18
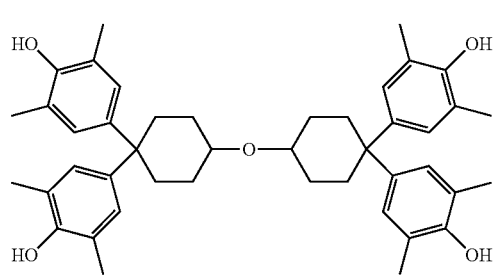
A-19
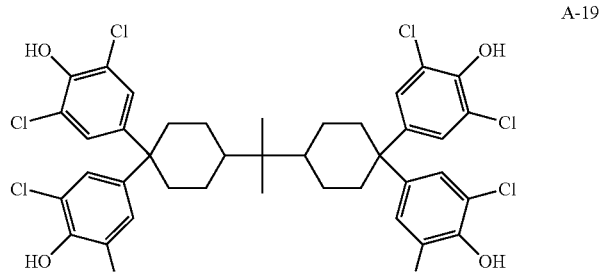

-continued
A-20
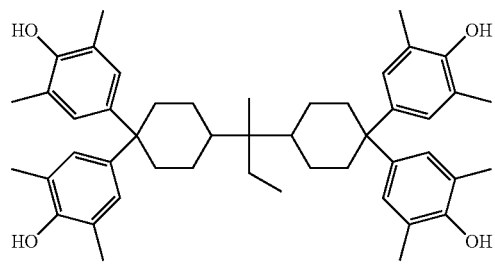
A-21
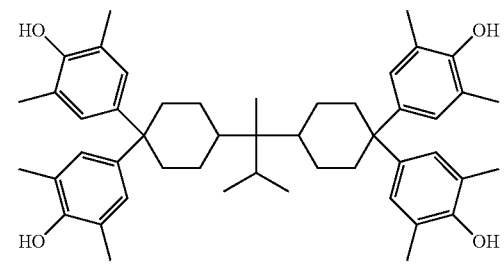
A-22
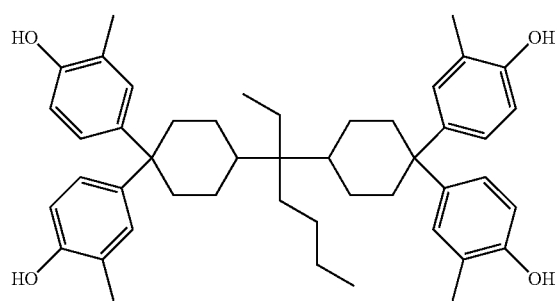
A-23
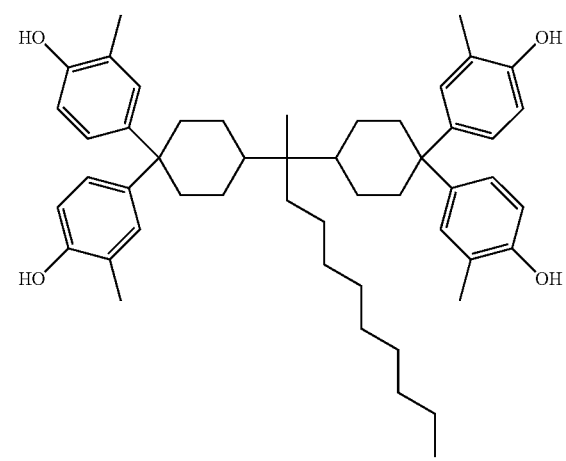
A-24
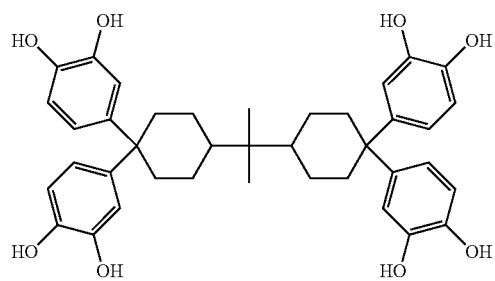
A-25
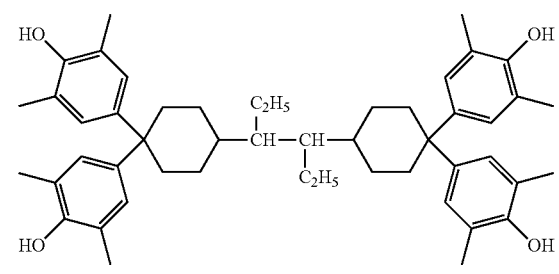
A-26
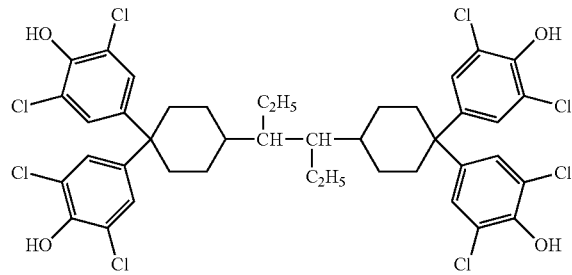
A-27
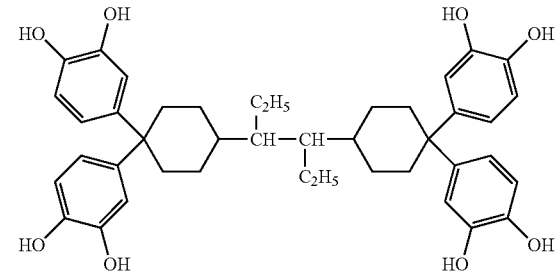

-continued

A-28

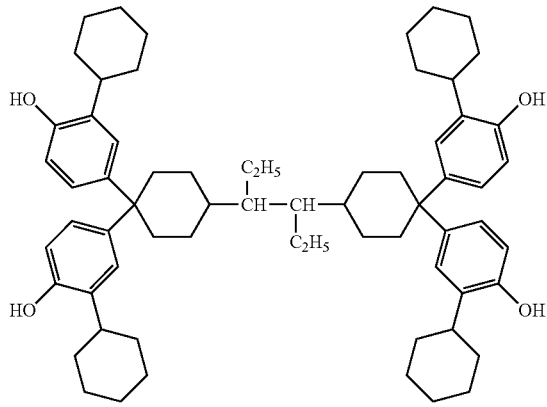

A-29

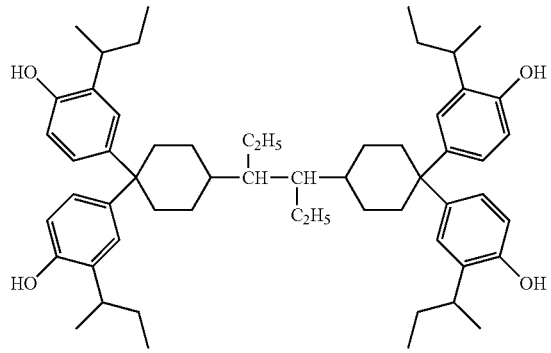

(Content of the Compound Represented by General Formula I)

It is preferable for the content of the compound represented by General Formula I in the resin composition of the present disclosure to be at least 10 parts by mass per 100 parts by mass of resin, and more preferably 20 parts by mass, from the viewpoint of moisture permeability. In addition, it is preferable for the content of the compound to be 50 parts by mass or less per 100 parts by mass of resin, and more preferably 40 parts by mass or less, from the viewpoint of compatibility.

The resin composition of the present disclosure is obtained by mixing the bis type alicyclic cardo phenol compound represented by General Formula I into a resin as an additive. According to such a configuration, the resin composition is that capable of forming a film having low haze, which is an index of transparency of the film, heat resistance greater than or equal to the heat resistance inherent to the resin and lower moisture permeability than the moisture permeability inherent to the resin.

<<Resin>>

The bis type alicyclic cardo phenols represented by General Formulae I and II, can exhibit the effect of imparting a low moisture permeability without causing deterioration of the transparency and the heat resistance of a resin regardless of the type of resin it is added to. However, it is preferable for the resin in the resin composition of the present disclosure to be a resin favorably suited for use as an optical film, and also preferably a resin which is capable of forming a film by solution film formation or by the solution casting method.

Preferable examples of such resins include cellulose ester resins, acrylic resins, polycarbonate resins, and cycloolefin resins.

Among these, acrylic resins can be used most preferably in the present disclosure, due to their superior transparency and low moisture permeability.

In the present disclosure, the resin but may be a single type of resin, or may be obtained by blending a plurality of kinds of resin. In addition to the preferable resins described above, the resin composition may also include resin additive components within a range that does not negate the advantageous effects of the present disclosure.

The acrylic resin preferably contains a structural unit derived from methyl methacrylate, and may or may not also include a structural unit derived from an alkyl (meth) acrylate other than methyl methacrylate.

In the acrylic resin, it is preferable for the content of structural units derived from methyl methacrylate to be 95 mass % or greater, more preferably 97 mass % or greater, and even more preferably 100 mass % in order to sufficiently exhibit the advantageous effects of the present disclosure, including heat resistance.

Examples of the alkyl(meth)acrylate other than methyl methacrylate include acrylic acid esters such as methyl acrylate, ethyl acrylate, n-butyl acrylate, isobutyl acrylate, t-butyl acrylate, cyclohexyl acrylate, benzyl acrylate (preferably alkyl acrylates with alkyl groups having carbon numbers within a range from 1 to 18), ester methacrylates such as ethyl methacrylate, propyl methacrylate, n-butyl methacrylate, isobutyl methacrylate, t-butyl methacrylate, cyclohexyl methacrylate, and benzyl methacrylate methacrylic acid esters (preferably alkyl methacrylates having alkyl groups with carbon numbers within a range from 1 to 18); and the like. These alkyl(meth)acrylates may be used singly or in combinations of two or more.

From the viewpoint of thermal decomposition resistance and fluidity of copolymers, methyl acrylate, ethyl acrylate, n-butyl acrylate, isobutyl acrylate, 2-ethylhexyl acrylate are preferable, and n-butyl methyl acrylate or acrylic acid are particularly preferable for use.

The acrylic resin used in the present disclosure may also comprise structural units other than those described above. Such structural units include α,β-unsaturated acids such as acrylic acid and methacrylic acid, unsaturated group-containing divalent carboxylic acids such as maleic acid, fumaric acid, and itaconic acid, aromatic vinyl compounds such as styrene and α-methyl styrene, α,β-unsaturated nitriles such as acrylonitrile and methacrylonitrile, maleic anhydride, maleimide, N-substituted maleimides, glutaric anhydride, and the like. These structural units may be introduced alone into the acrylic resin, or two or more kinds of the structural units may be combined and introduced into the acrylic resin.

In the case that an acrylic resin is employed as the resin, examples of resins that may be included as additive components include: olefin-based thermoplastic resins such as polyethylene, polypropylene, ethylene-propylene copolymer, and poly (4-methyl-1-pentene); halogen-containing thermoplastic resins such as polyvinyl chloride and chlorinated vinyl resin; acrylic thermoplastics such as polymethyl methacrylate; styrenic thermoplastic resins such as polystyrene, a styrene-methyl methacrylate copolymer, styrene-acrylonitrile copolymer, acrylonitrile-butadiene-styrene block copolymer; polyesters such as polyethylene terephthalate, polybutylene terephthalate, and polyethylene naphthalate; polyamides such as nylon 6, nylon 66, nylon 610; polyacetal; polycarbonates; polyphenylene oxide; polyphenylene sulfide; poly polyetheretherketone; polysulfone; polyethersulfone; polyoxyethylene benzyl alkylene; polyamideimide; polybutadiene rubber, and rubber polymers such as ABS resin and ASA resin blended with acrylic rubber. When adding a resin other than the acrylic resin in the acrylic resin composition, the resin to be added may be in a compatible state, or may be mixed without being dissolved.

Acrylic resins which are favorably suited for use in the resin composition of the present disclosure may be commercially available products or those obtained by known synthesizing methods that employ emulsion polymerization, solution polymerization, bulk polymerization, or suspension polymerization. Among such polymerization methods, emulsion polymerization and suspension polymerization are preferred. For suspension polymerization, it is possible to use an initiator used in ordinary suspension polymerization, examples of which include organic peroxides and azo compounds. In addition, known suspension stabilizers which are usually used can be employed. Examples of such suspension stabilizers include organic colloidal polymer substances, inorganic colloidal high molecular substances, inorganic fine particles and combinations of these with surfactants.

The resin composition of the present disclosure is favorably suited for use as a raw material composition for forming a film. Particularly, the resin composition of the present disclosure is favorably suited for use as a raw material composition (dope composition) which is coated on a support in the solution casting method. In the case that the resin composition of the present disclosure is employed as a dope composition, it is preferable for the resin composition of the present disclosure to further contain a solvent.

The content of solids in the dope composition (resin, the bis type alicyclic cardo phenol compound represented by General Formula I, and the sum of the additives and the like which are added, as necessary) is preferably 10 mass % or greater and 40 wt % or less, more preferably 10 mass % or greater and 30 mass % or less, and further preferably 15 mass % or greater and 25 mass % or less. By setting the content as such, the dope composition can be of a viscosity favorably suited for solution casting that enables obtainment of a high quality film having a desired thickness and a favorable surface profile in which fluctuations in thickness are suppressed. In the case that an acrylic resin is employed as the resin and the content of the solids is 22 mass % or less, peeling a film from a substrate is facilitated, by using the alcohol to be described later as a solvent.

In the following, many aspects of dope compositions as a resin will be described as examples in which acrylic resin compositions use acrylic resins which are superior from the viewpoints transparency and low moisture permeability. However, the resin in the resin composition is not limited to acrylic resins.

The solvent used in the dope composition is not particularly limited as long as it dissolves the resin in the resin composition of the present disclosure. It is preferable for the solvent to be that which is also capable of dissolving the bis type alicyclic cardo phenol compound represented by General Formula I and additives which are added as necessary.

When the resin is an acrylic resin, either chlorine series solvents having chlorine series organic solvents as the main solvent or non chlorine series solvents that do not have chlorine series organic solvents as the main solvent may be employed as an organic solvent. Two or more organic solvents may be used as a mixture.

When the resin is an acrylic resin, it is preferable for a chlorine series organic solvent to be used as a main solvent. In the present disclosure, the type of chlorine series organic solvent is not particularly limited as long as the objective of dissolving and casting the acrylic resin and additives contained in the acrylic resin composition can be achieved. Dichloromethane and chloroform are preferable as the chlorine series organic solvent. Dichloromethane is particularly preferable.

Furthermore, there is no particular problem in mixing in organic solvents other than chlorine series organic solvents. In this case, it is necessary for dichloromethane to be employed at an amount of at least 50 mass % in the total amount of the organic solvent. The other organic solvents used in combination with the chlorine series organic solvent in the present disclosure are described below. That is, preferred examples of other organic solvents are preferably solvents selected from esters having carbon numbers within a range from 3 to 12, ketones, ethers, alcohols, and hydrocarbons. The esters, ketones, ethers, and alcohols may have a cyclic structure. Compounds having two or more of esters, ketones, and ether functional groups (that is, —O—, —CO— or —COO—) may also be used as solvents. For example, such compounds may have other functional groups such as alcoholic hydroxyl groups. In the case that a solvent has two or more types of functional groups, the carbon number thereof may be within the range specified for the compound having any functional group.

Examples of esters having carbon numbers within a range from 3 to 12 include ethyl formate, propyl formate, pentyl formate, methyl acetate, ethyl acetate, and pentyl acetate. Examples of ketones having 3 to 12 carbon atoms include acetone, methyl ethyl ketone, diethyl ketone, diisobutyl ketone, cyclopentanone, cyclohexanone, and methyl cyclohexanone. Examples of ethers having carbon numbers within a range from 3 to 12 include diisopropyl ether, dimethoxymethane, dimethoxyethane, 1,4-dioxane, 1,3-dioxolane, tetrahydrofuran, anisole, and phenetole. Examples of organic solvents having two or more functional groups include 2-ethoxyethyl acetate, 2-methoxyethanol, and 2-butoxyethanol.

Examples of the alcohol to be used in combination with the chlorine series organic solvent may be a straight chain, branched, or cyclical. Among these alcohols saturated aliphatic hydrocarbons are preferable. The hydroxyl group of the alcohol may be any of primary to tertiary. Examples of the alcohol include methanol, ethanol, 1-propanol, 2-propanol, 1-butanol, 2-butanol, t-butanol, 1-pentanol, 2-methyl-2-butanol, and cyclohexanol. Note that a fluorine series alcohol may be employed as the alcohol. Examples of fluorine series alcohols include 2-trifluoroethanol, 2,2,2-trifluoroethanol, and 2,2,3,3-tetrafluoro-1-propanol. Further, the hydrocarbons may be straight chains, branched, or cyclic. Either aromatic hydrocarbons or aliphatic hydrocarbons may be employed. The aliphatic hydrocarbons may be saturated or unsaturated. Examples of the hydrocarbon include cyclohexane, hexane, benzene, toluene, and xylene.

The solvent disclosed in Japanese Unexamined Patent Publication No. 2007-140497 may be employed as the other solvent.

The solvent comprises a mixed solvent of (A) methylene chloride and (B) an alcohol having a carbon number within a range from 1 to 4. It is preferable for the mass ratio (A:B) of (A) and (B) in the mixed solvent to be within a range from 85:15 to 50:50. A:B is preferably within a range from 85:15 to 60:40, more preferably within a range from 85:15 to 70:30, and even more preferably within a range from 85:15 to 75:25. By setting A:B to be such a range, it is possible to obtain the advantageous effect of facilitating peeling of a saturated film from a substrate. The saturated film is a cast film (web) formed by casting a dope composition on a substrate, in a state which is sufficiently dry to be peeled off the substrate. Please refer to the method for producing a polarizing plate protective film to be described later for a description of the steps of a solution film formation process and each film during the process.

It is preferable for methanol, ethanol, or isopropanol to be employed as the alcohol (B) having a carbon number within a range from 1 to 4 in the solvent mixture. It is more preferable for methanol or ethanol to be employed as the alcohol (B), and it is most preferable for methanol to be employed as the alcohol (B).

(Weight Average Molecular Weight of the Acrylic Resin)

In the case that an acrylic resin is employed as the resin, the weight average molecular weight of the acrylic resin is not particularly limited. However, it is preferable for the weight average molecular weight of the acrylic resin to be within a range from 80,000 to 3,000,000 in order to sufficiently exhibit the advantageous effect of the present disclosure. It is more preferable for the weight average molecular weight of the acrylic resin to be within a range from 80,000 to 2,500,000, and even more preferably a range from 250,000 to 2,000,000. Acrylic resins with a weight average molecular weight in such a range have a weight average molecular weight higher than the weight average molecular weight of acrylic resins used in solution film formation, and are suitable for solution film formation.

If the weight average molecular weight of the acrylic resin is 80,000 or greater, the viscosity of the acrylic resin composition can be high even if the concentration of the acrylic resin in the acrylic resin composition is low (10 mass %, for example) low. As a result, it is possible to suppress stripes entering the cast film during ejection from a casting die. In addition, if the weight average molecular weight (Mw) of the acrylic resin is 80,000 or greater, elongation at break of an acrylic resin film formed thereby when not stretched will increase, and handling suitability during film production will be improved.

The weight average molecular weight of the acrylic resin being 3,000,000 or less is preferable from the viewpoint of a polymerization process.

Note that the "weight average molecular weight (Mw)" as used in the present disclosure, is the weight-average molecular weight measured by gel permeation chromatography under the following conditions.
Solvent: Tetrahydrofuran
Device name: TOSOH HLC-8220GPC
Columns: TOSOH TSKgel Super HZM-H (4.6 mm×15 cm) 3 connected and used
Column temperature: 25° C.
Sample concentration: 0.1% by mass
Flow rate 0.35 ml/min
Calibration curve: a calibration curve obtained by 7 samples of TOSOH TSK standard polystyrene Mw=2800000-1050 was utilized.

[Compound for Preventing Oxidation of the Compound Represented by General Formula I]

From the viewpoint of suppressing coloration, it is preferable for the resin composition of the present disclosure to include a compound that prevents oxidation of the compound of General Formula I within a range that does not negate the advantageous effects of the present disclosure.

It is preferable for the compound for preventing oxidation of the compound of General Formula I to be phenol-based antioxidants, sulfur-based antioxidants, or amide-based antioxidants. Specific examples of the compound for preventing oxidation of the compound of General Formula I are shown below. However, the present disclosure is not limited to these examples.

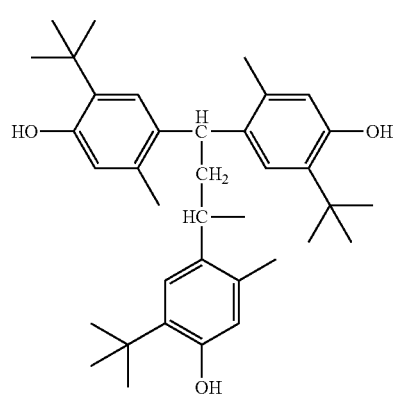

B-1

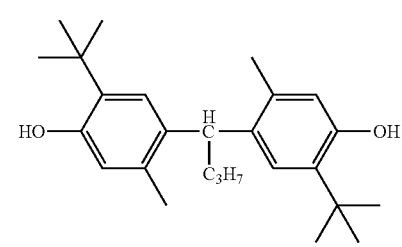

B-2

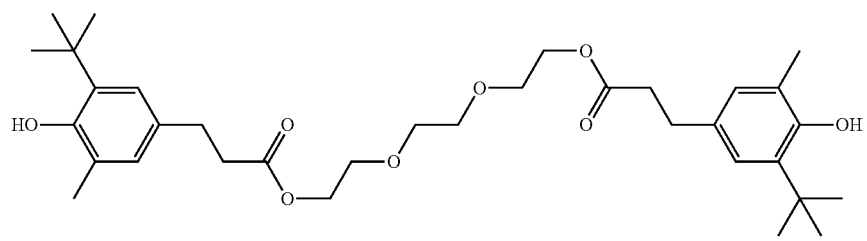

B-3

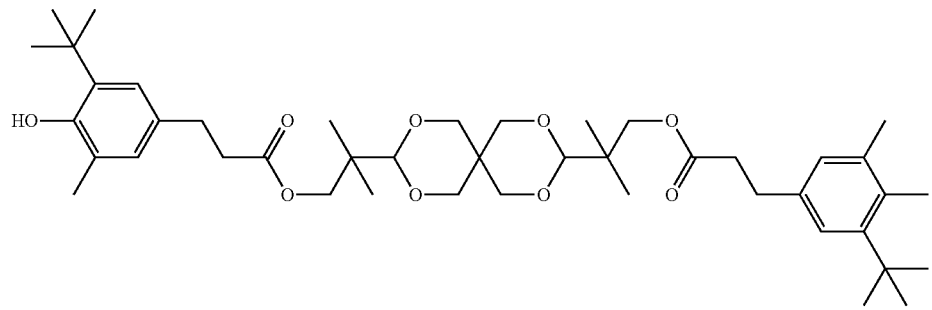
B-4
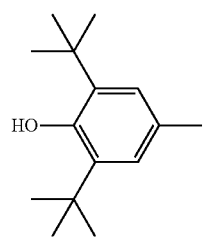
B-5
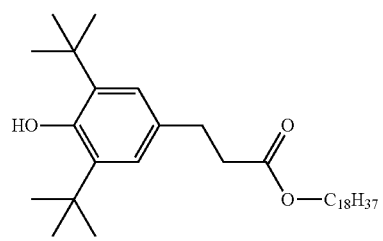
B-6
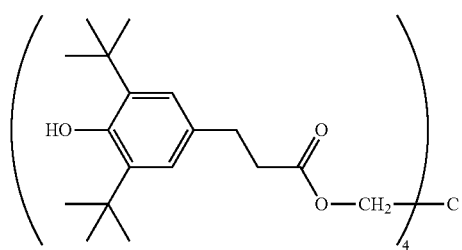
B-7
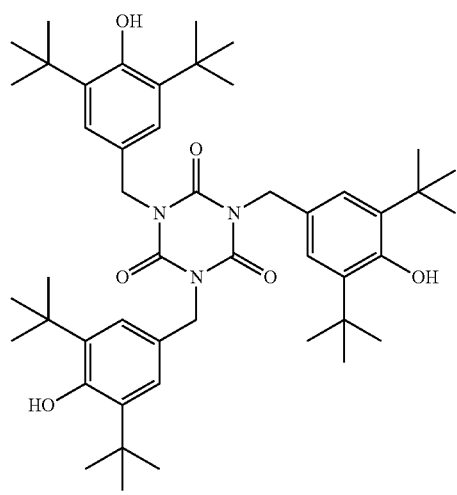
B-8
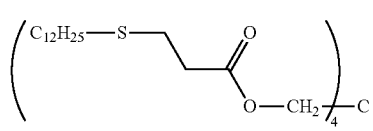
B-9
B-10
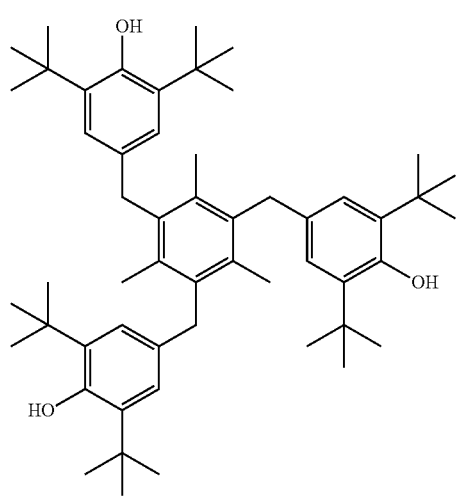

-continued
B-11
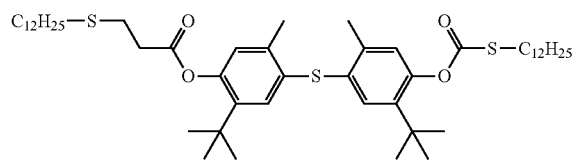
B-12
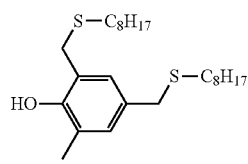
B-13
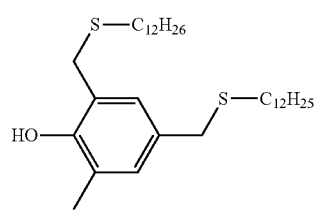
B-14
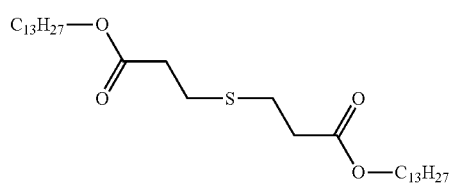
B-15
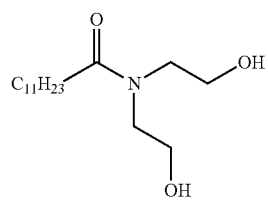
B-16
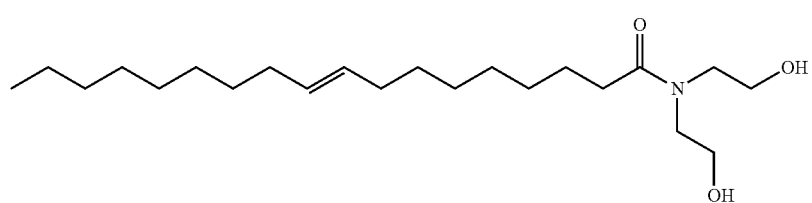
B-17
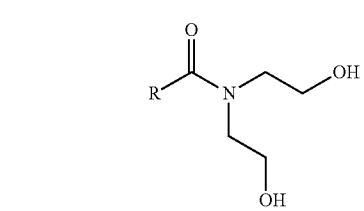
R = $C_7H_{15}/C_9H_{19}/C_{11}H_{23}/C_{13}H_{27}/C_{14}H_{29}/C_{17}H_{35}/C_{17}H_{33}/C_{17}H_{31}$
= 7.8/7.6/44.8/18.1/9.5/2.4/8.2/1.5
B-18
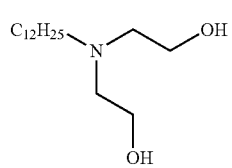
B-19
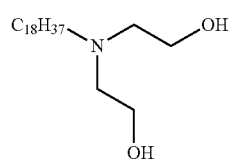
B-20
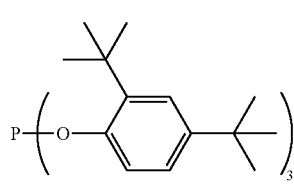
B-21
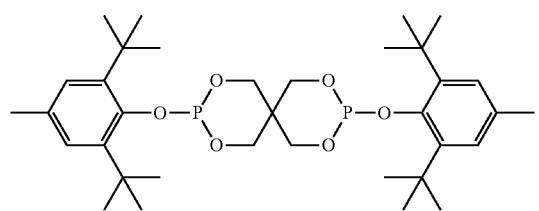
B-22

-continued

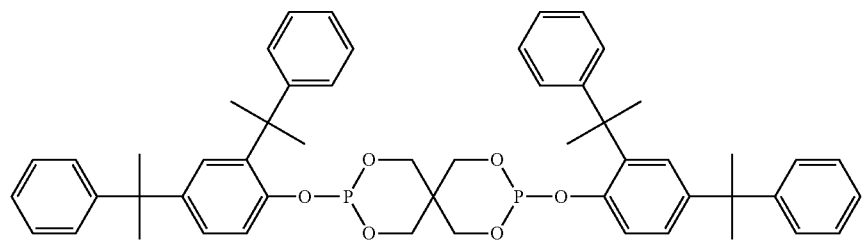
B-23

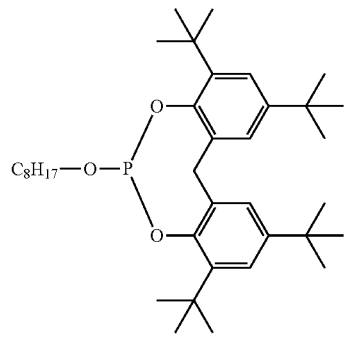
B-24

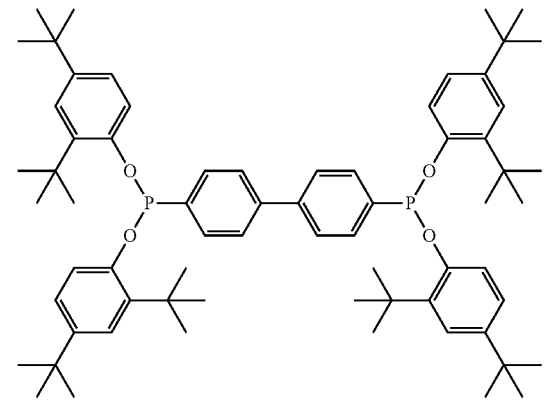
B-25

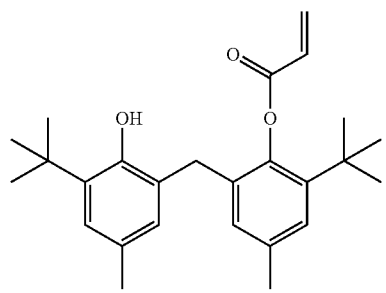
B-26

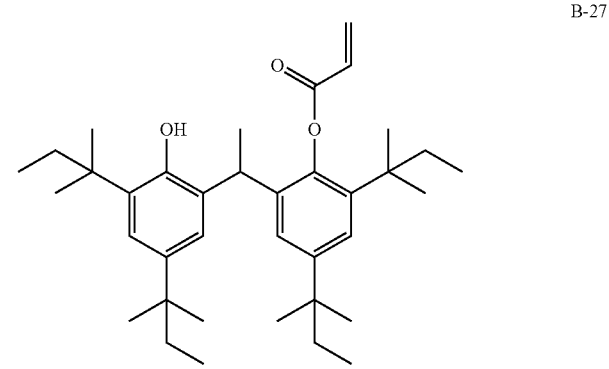
B-27

Commercially available compounds may be favorably employed as compounds for preventing oxidation of the compound of General Formula I.

From the viewpoint of suppressing coloration, it is preferable for the content of the compound for preventing oxidation of the compound of General Formula I in the resin composition of the present disclosure to be 0.1 parts by mass or greater relative to compound 100 parts by mass of the compound represented by General Formula I, and more preferably 0.5 parts by mass or greater. From the viewpoint of moisture permeability, it is preferable for the content of the compound for preventing oxidation of the compound of General Formula I in the resin composition of the present disclosure to be 5 parts by mass or less, and more preferably 2 parts by mass or less.

The resin composition of the present disclosure may also include one or more of a plasticizer, an ultraviolet absorber, an antioxidant, a brittleness modifier, and an optical expression agent as additives, within a range that does not negate the advantageous effects of the present disclosure.

A plasticizer has a function of improving the fluidity and flexibility of the dope composition. An antioxidant may be added as appropriate as long as it is a compound that prevents the oxidation of the resin composition of the present disclosure. A vinyl group-containing phenolic antioxidant capable of capturing alkyl radicals which are generated in the initial stages of autoxidation of resins, for example, SUMILIZER GM manufactured by Sumitomo Chemical Co., Ltd., is preferable as an antioxidant. Since the antioxidant for the compound represented by General Formula I are operating mechanisms that capture or decompose peroxide radicals which are generated in the middle to late stages of autoxidation of resins, advantageous effects can be expected if an antioxidant that is suitable for each stage is added.

<Film Obtained by Forming the Resin Composition into a Film>

The film of the present disclosure is that which is formed using the resin composition of the present disclosure, and preferably that which is formed using the acrylic resin composition of the present disclosure. A film obtained by solution casting the acrylic resin composition of the present disclosure has low haze, which is an index of transparency of the film, heat resistance greater than or equal to the heat resistance inherent to the resin and lower moisture permeability than the moisture permeability inherent to the resin. Because the film of the present disclosure has favorable heat resistance is good it can be efficiently produced and is useful in various applications. The film of the present disclosure is particularly favorably suited for use as an optical film such as a polarizing plate protective film and an optical compensation film.

Furthermore, a film formed by using the resin composition of the present disclosure may have additional structures, depending on its use. Examples of such structures include surface treatments administered on the surface of the film and a functional layer or the like provided on the surface of the film.

As described above, the resin composition of the present disclosure is favorably suited for use as a dope composition in solution film formation. Therefore, the film of the present disclosure is preferably formed by solution casting.

Solution casting is executed by after casting a dope composition on a substrate on which a film is to be formed, then drying the cast film (web). The details will be described in connection with a manufacturing process for a polarizing plate protective film to be described later. In solution casting, the drying process greatly influences the quality of the film. Therefore, it is preferable for a guideline for a drying time to be measured in advance.

An embodiment of a polarizing plate protective film of the present disclosure obtained by forming the resin composition of the present disclosure into a film, as well as a polarizing plate and a liquid crystal display device equipped with the polarizing plate protective film will be described with reference to the attached drawings. Note that in the drawings of the present specification, the scales of the components are changed as appropriate to facilitate visual understanding.

<Polarizing Plate Protective Film, Polarizing Plate, and Liquid Crystal Display Device>

FIG. 1 is a schematic diagram showing the structure of a liquid crystal display device 1 according to an embodiment of the present disclosure. As illustrated in FIG. 1, the liquid crystal display device 1 includes a pair of polarizing plates (an upper polarization plate 10 and a lower polarizing plate 18), and a liquid crystal cell 2 sandwiched between the pair of polarizing plates, a liquid crystal cell 2. The liquid crustal cell 2 includes a liquid crystal layer 15, an liquid cell upper electrode substrate 13 and a liquid crystal cell lower electrode substrate 16 provided above and below the liquid crystal layer 15.

In the case that the liquid crystal display device 1 is of the transmission type, the aspect will be that in which the upper polarizing plate 10 is designated as a front side (viewing side) polarization plate, the lower polarizing plate 18 is designated as a rear side (backlight side) polarization plate, and although not shown, a back light unit is provided under the rear side polarizing plate 18, and a color filter is provided between the liquid crystal layer 15 and the front side polarizing plate 10. In FIG. 1, reference numerals 12 and 19 respectively denote the directions of absorption axes which are substantially perpendicular to each other, and reference numerals 14 and 17 denote orientation control directions of the electrode substrates.

In the liquid crystal display device 1, at least one of the pair of polarizing plates (10, 18) is a polarizing plate of the present disclosure equipped with a polarizer and polarizing plate protective film of the present disclosure provided on at least one surface of the polarizer.

FIG. 2 is a cross sectional view in the thickness direction showing the configuration of the upper polarizing plate 10. As illustrated in FIG. 2, the upper polarizing plate 10 is of a configuration in which a polarizer 100 is sandwiched between two polarizing plate protective films 110 and 120.

In the present embodiment, the polarizing plate protecting film 120 on the side of the liquid crystal cell is provided with an optically anisotropic layer 130 on the side of the liquid crystal cells. The lower polarizing plate 18 is of a configuration in which the stacking direction of each layer is vertically inverted from that of the upper polarizing plate 10.

The polarizing plate protective film 110 provided on the viewing side is provided at the exterior portion of the liquid crystal display device, and therefore it is preferable for the polarizing plate protective film 110 to have a lower moisture permeability. Accordingly, the polarizing plate protective film 110, is that having at least one layer of the film of the present disclosure formed by using the resin composition of the present disclosure. It is preferable for the polarizing plate protective film 110 to have at least one layer of one layer of the film of the present disclosure formed by using the resin composition of the present disclosure in an aspect that employs an acrylic resin as the resin.

The moisture permeability level required of the polarizing plate protective film 120 on the liquid crystal cell side is lower compared to that for the polarizing plate protective film 110 on the viewing side. However, the polarizing plate protective film 120 on the liquid crystal cell side may include at least one layer of the film of the present disclosure formed by using the resin composition of the present disclosure.

The polarizing plate 10 may be produced by a common method. For example, there is a method in which an obtained polarizing plate protecting film undergoes alkali treatment, and adhered to both sides of the polarizer, which is produced by stretching and immersing a polyvinyl alcohol film prepared by being immersed and stretched in an iodine solution, using a completely saponified polyvinyl alcohol solution. Instead of the alkali treatment, a simplified adhesion processing may be performed as described in Japanese Unexamined Patent Publication Nos. 6(1994)-094915 and 6(1994)-118232. In addition, the aforementioned surface treatment may also be administered.

Examples of the adhesive used to bond the polarizing plate protective film treated surface and the polarizer include polyvinyl alcohol-based adhesives such as polyvinyl alcohol, polyvinyl butyral, and vinyl-based latexes such as butyl acrylate.

The polarizing plate protective film 110 and the polarizer 100 may be bonded with other adhesives or pressure sensitive adhesives, or may be laminated directly without an adhesive or a pressure-sensitive adhesive.

The polarizer 10 and the liquid crystal display device 1 are equipped with the film having low haze, heat resistance greater than or equal to the heat resistance inherent to the resin. Therefore, the polarizer 10 and the liquid crystal device 1 are a polarizer and a liquid crystal device in which deterioration due to moisture absorption is low.

<<Polarization Plate Protective Film>>

The polarizing plate protective film 110 is equipped with at least one layer of the film of the present disclosure formed using the resin composition of the present disclosure. The polarizing plate protective film 110 is preferably equipped with only a single layer of the film of the present disclosure.

In addition, the polarizing plate protective film 110 may be of a multilayer structure having layers other than the film of the present disclosure. Further, the polarizing plate protective film 110 may be subjected to surface treatment or provided with a functional layer or the like. However, the film of the present disclosure is a film having low haze, which is an index of transparency, superior heat resistance, and low permeability. Therefore, it is preferable for the polarizing plate protective film 110 to be of a configuration equipped with the film of the present disclosure as the outermost layer (a layer having an interface with air). Here, an aspect in which the polarizing plate protective film 110 is configured by a single layer of the film of the present disclosure will be described.

It is preferable for the moisture permeability of the polarizing plate protective film 110 in a liquid crystal display device to which the polarizing plate protective film is applied to be 150 g/m$^2$/day or less as a 40 μm converted value, more preferably 70 g/m$^2$/day or less as a 40 μm converted value, even more preferably 50 g/m$^2$/day or less as a 40 μm converted value, and still more preferably 40 g/m$^2$/day or less as a 40 μm converted value, from the viewpoint of suppressing warping of a liquid crystal cell and display unevenness when displaying black after being exposed to a normal temperature, high humidity environment and a high temperature, high-humidity environment over time If such moisture permeability requirements are satisfied, the film thickness of the polarizing plate protective film 110 is not particularly limited. However, it is preferable for the film thickness to be within a range from 10 μm to 60 μm, more preferably a range from 10 μm to 50 μm, and even more preferably a range from 20 μm to 50 μm.

The "moisture permeability as a 40 μm converted value" of the polarizing plate protective film in the present specification is a standardized value of the moisture permeability of a film as measured according to the method defined in JIS Z-0208 under conditions of a temperature at 40° C. and 90% relative humidity, then converted assuming that the film thickness is 40 μm. The conversion of the film thickness is carried out according to the following formula.

Formula:  Moisture Permeability as 40 μm Converted Value=Measured Moisture Permeability×Measured Film Thickness (μm)/40 (μm)

In the polarizing plate protective film 110, the optical performance will improve as the total haze value is lower. However, it is preferable for the total haze value to be 0.01% or greater and 2.00% or less, more preferably 1.00% or less, even more preferably 0.50% or less, still more preferably 0.30% or less, and most preferably 0.20% or less, taking material selection, production management, and handling properties of rolled film into consideration. If the total haze value is 2.00% or less, the transparency of the film will be high, which is effective in improving the contrast ratio and brightness of the liquid crystal display device.

The "haze value" of the polarizing plate protective film in the present specification is a total haze value and an internal haze value of a 40 mm×80 mm sample cut out from a polarizing plate protective film measured in accordance with the method specified in JIS K-6714 at a temperature of 25° C. and a relative humidity of 60%. The haze value can be measured using a haze meter (manufactured by Suga Test Instruments Co., Ltd., trade name HGM-2DP).

As described above, the polarizing plate protective film 110 is a film having low haze, which is an index of transparency, favorable heat resistance, and low moisture permeability. Therefore, it is possible to achieve the moisture permeability and haze values above. The total haze and the internal haze can be adjusted by the types and amounts of the resin or oligomer of the resin composition (particularly the weight-average molecular weight), the types and amounts of other additives, and further by film production conditions (temperature during stretching, stretching ratio, etc.).

[Method of Producing Polarizing Plate Protective Film]

Next, a method of producing a polarizing plate protective film 110 will be described with a solution film formation method as an example. The solution film formation method comprises at least a dope preparation step of preparing the resin composition of the present disclosure obtained by dissolving a resin and the compound represented by General Formula I (dope composition) in a solvent, a casting step of casting the dope composition on a substrate to form a cast film, and a peeling step of peeling the cast film from the substrate after the cast film dries.

After the peeling step, the peeled film may be subjected to a drying step for eliminating residual solvent (volatile portion) by further drying, and may also be subjected to a stretching step of stretching the film in at least a uniaxial direction, if necessary.

Each of the steps will be described below.

FIG. 3 is a schematic view showing one embodiment of a production line for polarizing plate protective films which is capable of performing these processes continuously. However, the film production line for use in the production method of the present disclosure is not limited to that illustrated in FIG. 3. Note that in the manufacturing line of the film a "saturated film", a "dry film" which is the saturated film after drying, and a "stretched film" which is the dry film after stretching, are obtained. The cast film according to the present disclosure will encompass all of these films from after casting and before a peeling step (the "saturated film", the "dry film" and the "stretched film"), and the film of the present disclosure encompasses all of these films after the film is peeled off of the substrate (the "saturated film", the "dry film" and the "stretched film").

The film production line 20 shown in FIG. 3 is provided with a stock tank 21, a filtration device 30, a casting die 31, a metal support 34 placed on rollers 32 and 33 and a tenter drying device 35. The production line 20 is further provided with an edge cutting device 40, a drying chamber 41, a cooling chamber 42, a winding chamber 43, and the like.

A stirrer 61 rotated by a motor 60 is mounted in the stock tank 21. The stock tank 21 is connected with the casting die 31 via a pump 62 and the filtration device 30.

The width of the casting die 31 is preferably 1.1 times to 2.0 times the width of the film, which is to be the finished product.

The metal support 34 is placed on the rollers 32 and 33 beneath the casting die 31. The rollers 32 and 33 are rotated by a driving device (not shown), and the metal support 34 is conveyed by this rotation.

It is preferable for a heat transfer medium circulator 63 to be mounted on the rollers 32 and 33 to cause the surface temperature of the metal support 34 to be a predetermined value. It is preferable for the metal support 34 to be that of which the surface temperature can be adjusted to be within a range from −20° C. to 40° C.

It is preferable for the width of the metal support 34 to be 1.1 to 2.0 times the range of the casting width of the dope composition 22. In addition, it is preferable for the metal support 34 to have a length within a range from 20 m to 200 m, a thickness within a range from 0.5 mm to 2.5 mm, and for the metal support 34 to be polished such that the surface roughness thereof is 0.05 μm or less. It is preferable for the metal support 34 to be made of stainless steel, and more preferably made of SUS316 so as to have sufficient strength and resistance to corrosion. In addition, it is preferable for a metal support having a non uniformity in film thickness of 0.5% or less to be employed as the metal support 34.

The casting die 31, the metal support 34, and the like are housed in a casting chamber 64. A temperature controller 65 for maintaining the interior temperature of the casting chamber 64 at a predetermined value and a condenser 66 for condensing and recovering volatilized organic solvent are provided in the casting chamber 64. A recovering device 67 for recovering the condensed organic solvent is provided at the exterior of the casting chamber 64. In addition, it is preferable for a decompression chamber 68 for controlling the rear surface portion of a cast bead which is formed from the casting die 31 through a metal support 34 with pressure to be provided. The present embodiment is equipped with the decompression chamber 68.

Air blowing ports 70, 71, 72, and 73 for evaporating the solvent in the cast film 69 are provided near the peripheral surface of the metal support 34.

A blower 81 is provided in a transfer section 80. A crusher 90 for finely cut and process debris of the lateral end portions (referred to as "ears") of cut off film 82 is connected to the edge cutting device 40 which is downstream of the tenter drying device 35.

The drying chamber 41 is provided with a great number of rollers 91, and a adsorption recovery device 92 for adsorbing solvent vapor generated by evaporation is provided in the drying chamber 41. A forced neutralization device (neutralizing bar) for adjusting the charged voltage of the film 82 to be within a predetermined range (−3 kV to +3 kV, for example) is provided downstream of the cooling chamber 42. Further, in the present embodiment, knurling roller 94 for providing knurling by embossing both edges of the film 82 is provided as appropriate downstream of the forced neutralization device 93. A winding roller 95 for winding the film 82 and a press roller for controlling the tension during the winding are provided inside the winding chamber 43.

Next, an example of a method for producing the film 82 using the film production line (referred to as a band manufacturing apparatus) 20 described above will be described.

A dope composition 22 is constantly uniformized by the rotation of the stirrer 61. Additives such as a retardation enhancer, a plasticizer, and an ultraviolet absorber may be mixed into the dope composition 22 during this stirring operation.

(1) Dope Preparation Process

The dope preparation process is a process for preparing the resin composition of the present disclosure (the dope composition). It is preferable for the dope preparation process of the present disclosure to be that in which resin and additives are dissolved in an organic solvent having a good solvent for the resin as its main component while being stirred in a melting kettle, or that in which an additive solution is mixed into a resin solution to form the dope.

With respect to the material of the dope composition, please refer to the description of the section <Resin Composition> above.

It is preferable for the dope composition to be prepared at a temperature of 0° C. or greater (ordinary temperature or high temperature). Preparation of the dope composition can be performed using a method and apparatus for preparing dope in an ordinary solvent casting method.

To dissolve the polymer, various dissolving methods such as a method carried out at normal pressure, a method carried out at the boiling point of the main solvent or less, a method carried out under pressure at the boiling point of the main solvent or greater, a cooling dissolution method as disclosed in Japanese Unexamined Patent Publication Nos. 9(1997)-095544, 9(1997)-095557, and 9(1997)-095538, and the method carried out under high pressure as disclosed in Japanese Unexamined Patent Publication No. 11(1999)-021379 may be employed. From the viewpoint of dissolution efficiency, a method carried out under pressure at the boiling point of the main solvent or greater is preferable. In this case, the acrylic resin, the solvent (A) and a solvent and (B) are placed and sealed in a pressurized container, and stirred at the boiling point of the solvent or greater at room temperature under pressure and while heating to a temperature range where the solvent does not boil.

In the case that heat is applied, the temperature is usually 40° C. or greater, preferably within a range from 60° C. to 200° C., and more preferably a range from 80° C. to 110° C.

It is preferable for the concentration of the acrylic resin in the dope composition to be within a range from 10 mass % to 40 mass %. It is preferable for additives to be added during dissolution or after dissolution of the dope composition, for further dissolution and dispersion to be performed, for the dope composition to be filtered through a filter medium, then defoamed and sent it to the next step by a liquid feed pump.

(2) Casting Process

The casting process is a process for forming a cast film by casting the above dope composition onto a metal support. The dope composition 22 is sent to the filtration device 30 by the pump (a pressurized metering gear pump, for example) 62, then is cast from the casting die 31 onto the metal support 34.

A casting bead is formed from the casting die 31 through the metal support 34, and a cast film 69 is formed on the metal support 34. It is preferable for the temperature of the dope composition 22 at the time of casting to be within a range from −10° C. to 57° C.

The Cast film 69 moves accompanying the movement of the metal support 34. It is preferable for the casting die 31 to be a pressurizing die in which it is possible to adjust the slit shape of the base part to facilitate uniformization of film thickness. Examples of pressurizing dies include a coat hanger die and a T die, either type of die may be favorably employed. The surface of the metal support is a mirror surface. Two or more pressurizing dies may be provided above the metal support in order to accelerate film formation speed, and the dope composition may be divided and overlaid. Alternatively it is also preferable for a film having a laminated structure to be obtained by a co-casting method that simultaneously casts a plurality of dope compositions.

(3) Solvent Evaporation Process

Next, the cast film 69 is conveyed continuously to a location beneath the air blowing port 73. Drying air from the nozzles of the air blowing port 73 is blown toward the cast film 69. It is preferable to include a solvent evaporation process between the casting process and the peeling process. The solvent evaporation process is a process that heats the cast film (also referred to as web: a state before the film is finished, and still contains a large amount of solvent) on the metal support and causes the solvent to evaporate until it becomes possible to peel the web from the metal support.

Examples of methods for evaporating the solvent include a method in which air is blown from the side of the web and/or heat is transferred by a liquid from the underside of the metal support, and a method in which radiant heat is transferred to both sides of the web. The underside liquid heat transferring method is preferable due to its favorably drying efficiency. Also, combinations of the above methods are also preferable. In the case of the underside liquid heat transferring method, it is preferable for heating to be performed to a temperature at the boiling point of the main solvent of the organic solvent utilized in the dope composition or less, or a temperature at the boiling point of the solvent having the lowest boiling point among the organic solvents utilized in the dope composition or less.

(4) Peeling Process

The peeling process is a process for obtaining a film by peeling the cast film (web) 69 from the metal support after it dries. As a result of solvents evaporating by drying, the web 69 is peeled off of the metal support 34 at a stage when it becomes a film (saturated film) having self-supporting properties while being supported by a peeling roller 75 as a saturated film 74. The peeled saturated film 74 is sent to the next process. Note that peeling will become difficult if the amount of residual solvent (the formula below) in the web 69 is excessively great. Conversely, if the web 69 is peeled after it is excessively dried on the metal support, a portion of the web may tear during the peeling process.

It is preferable for the web 69 to be peeled from the metal support with the amount of residual solvent within a range from 5% by mass to 150% by mass, and more preferably within a range from 10% by mass to 120% by mass. The amount of residual solvent during peeling differs depending on the intensity of the drying conditions, the length of the metal support, etc. Therefore, it is preferable for a guideline for a drying time to be measured in advance, and for a preferred amount of residual solvent to be determined. If peeling is performed at a point in time at which the amount of residual solvent is high, the amount of residual solvent at the time of peeling is determined based on a balance of productivity and quality. In the present disclosure, it is preferable for the temperature at the peeling position on the metal support to be within a range from −50° C. to 40° C., more preferably a range from 10° C. to 40° C., and most preferably a range from 15° C. to 30° C.

The amount of residual solvent can be expressed by the following equation.

$$\text{Amount of Residual Solvent (mass \%)} = [(M-N)/N] \times 100$$

Here, M is the mass at any point in the web, N is the mass when the mass M is dried for 3 hours at 110° C.

(5) Drying Process (Heat Treatment Process), Stretching Process

The peeled saturated film 74 is sent to the tenter drying device 35 by the transfer section 80 having a great number of rollers. The drying of the saturated film 74 progresses in the transfer section 80 by blowing drying air at a desired temperature from the blower 81 in the transfer section 80. It is preferable for the temperature of the drying air to be within a range from 20° C. to 250° C.

It is preferable for the tenter drying device 35 to include a gripping member (clips, for example) for gripping both side ends of the saturated film 74 and partitioned areas at different temperatures. Solvent is evaporated to dry the saturated film 74 while it is conveyed by both side ends thereof being held by the gripping member inside the tenter drying device 35. It is preferable for the tenter drying device 35 to be provided with partitioned areas having different temperatures such that the saturated film 74 can be dried while adjusting drying conditions.

It is common to blow hot air to both sides of the saturated film 74 as a drying means. However, there is also means to heat and dry the saturated film 74 by applying microwaves instead of hot air. The temperature, the air blowing rate, and time required for drying differ depending on the solvent which is utilized. Drying conditions may be selected as appropriate according to the types and combinations of the solvents which are utilized.

It is preferable for the saturated film 74 to be stretched in a width direction (Transverse Direction, TD direction) perpendicular to a conveyance direction (Machine Direction, MD direction) in the transfer section 80 and/or the tenter drying device 35. By stretching the saturated film 74 unevenness which is generated while drying on the support and during peeling can be reduced, and a favorable surface shape can be obtained within the plane of the film. The stretching ratio in the width direction is preferably 10% or greater, more preferably 20% or greater, even more preferably within a range from 30% to 80%, and particularly preferably within a range from 40% to 60%.

Stretching may be carried out in the MD direction as well. In this case, stretching can be carried out by imparting a draw tension to the conveying direction to the saturated film 74 by causing the rotational speed of the rollers on the downstream side to be greater than the rotational speed of the rollers on the upstream side in the transfer section 80.

In the case of bidirectional stretching, it is preferable for stretching to be carried out in order with the MD direction first, and the TD direction second.

The stretching ratio in the MD direction is preferably within a range from 30% to 80%, and particularly preferably within a range from 40% to 60%. The stretching ratio (elongation) of the web during stretching can be achieved by a peripheral speed difference between the peeling speed (peeling roll draw) and the speed of the metal substrate. For example, in the case that a device having two nip rolls is employed, the film can be favorably stretched in the transport direction (longitudinal direction) by setting the rotational speed of the nip roll at the outlet end to be faster than the rotational speed of the nip roll at the inlet end.

Note that the term "stretching ratio (%)" as used herein refers to ratios obtained by the following equation.

$$\text{Stretching Ratio (\%)} = 100 \times \{(\text{length after stretching}) - (\text{length before stretching})\}/\text{unstretched length}$$

Stretching may be performed after the unstretched saturated film 74 is dried in the transfer section 80 and/or the tenter drying device 35 such that the amount of residual solvent in the film is 3.0 mass % or less, preferably 1.0 mass % or less, more preferably 0.5 mass % or less, even more preferably 0.3 mass % or less, and particularly preferably 0.2 mass % or less. However, it is preferable for the film at the time of stretching to be a saturated film. In the case that a film is produced without stretching, it is preferable for the film to be produced under conditions such that the thickness of the film is within a range from 10 μm to 200 μm, more preferably a range from 10 μm to 150 μm, even more preferably a range from 10 μm to 100 μm, and most preferably a range from 10 μm to 60 μm.

In the case that a polymer film in which the residual solvent amount is 3.0% by mass or less is stretched, stretching may be performed after winding the film once in an unstretched state.

In addition, only drying may be carried out in the transfer section 80 and/or the tenter drying device 35 after stretching the saturated film 74 first.

The saturated film 74 is sent to the downstream side of the tenter drying device 35 as the film 82 after being dried to a predetermined residual solvent content (volatile component). The edges of both side ends of the film 82 are cut off by the edge cutting device 40. The cut side edge portions are sent to the crusher 90 by a cutter blower (not shown). The crusher 90 crushes the cut off end portions of the film to form chips. These chips are reused to prepare a dope composition, and therefore this method is effective in terms of cost. Note that it is also possible to omit the process of cutting both side ends of the film. However, it is preferable for the cutting process to be carried out during any of the foregoing casting step to the step of winding the film.

The film 82, of which the side edge portions are cut off, is sent to the drying chamber 41 and is dried further. The temperature of the drying chamber 41 is preferably within a range from 50° C. to 160° C. In the drying chamber 41, the film 82 is conveyed while being wound around the roller 91, and solvent vapor generated by evaporation is adsorbed and recovered by the adsorption recovering device 92. Air, from which solvent components have been removed, is blown again as dry air in the interior of the drying chamber 41. Note that it is preferable for the drying chamber 41 to be divided into a plurality of compartments in order to vary drying temperatures.

The film 82 is cooled to approximately room temperature in the cooling chamber 42. Note that a humidification chamber (not shown) may be provided between the drying chamber 41 and the cooling chamber 42. In the case that the humidity control chamber is provided, it is preferable for air which is adjusted to have a desired humidity and temperature to be blown onto the film 82. Thereby, it will become possible to suppress curling of the film 82 and the occurrence of winding defects that occur during winding.

Furthermore, it is preferable for the knurling roller 94 to be provided, to provide knurling by embossing both edges of the film 82 in the present disclosure. The width of knurling is preferably within a range from 3 mm to 50 mm, and more preferably a range from 5 mm to 30 mm. The height of knurling is preferably within a range from 0.5 µm to 500 µm, and more preferably a range from 1 µm to 200 µm. The knurling roller 94 may provide knurling only on one surface or the film, or may provide knurling on both surfaces of the film.

(6) Winding

Finally, the film 82 is wound by the winding roller 95 in the winding chamber 43. At this time, it is preferable for the film 82 to be wound while applying a desired tension with a press roller 96. Note that it is preferable for the tension to gradually change from when winding is initiated until winding is completed. It is preferable for the length of the film obtained in the above manner to be wound at 100 m to 10000 m per roll, more preferably 500 m to 7000 m per roll, and even more preferably 1000 m to 6000 m per roll. The width of the film is preferably within a range from 0.5 m to 5.0 m, more preferably a range from 1.0 m to 3.0 m, and still more preferably a range from 1.0 m to 2.5 m.

The polarizing plate protective film 110 can be obtained by the processes described above.

When casting the dope composition in the solution casting method, it is also possible to co-cast two or more dope compositions as simultaneous streams or as sequential streams. The two co-casting methods may also be combined. When co-casting two or more dope compositions as simultaneous streams a casting die fitted with a feed block or a multiple manifold type casting die may be employed. Co-casting enables obtainment of a film consisting of multiple layers. In the multilayer film, it is preferable for at least one of the thickness of the layer toward the air surface and the thickness of the layer toward the substrate to be within a range from 0.5% to 30% of the total film thickness. Furthermore, in the case of co-casting, it is preferable for a high-viscosity dope composition is preferably enveloped in a lower viscosity dope composition when casting the dope compositions through a die slit onto a metal support.

Structures such as the casting die, the decompression chamber, and the metal support, co-casting, peeling, stretching, drying conditions in each process, handling methods, curl, winding methods after flatness correction, solvent recovery processes, and film collection methods are described in detail in paragraphs [0617] through [0889] of Japanese Unexamined Patent Publication No. 2005-104148.

In the above, an example of a method for manufacturing a polarizing plate protective film of the present disclosure is a doped composition described in the example was cast on a metal support in the casting process, dope composition in the casting step also hold a similar mechanism when it was cast on a drum. In this case devices and manufacturing conditions described in Japanese Unexamined Patent Publication No. 2013-082192 are preferably used.

<Optical Compensation Film>

The film of the present disclosure may be used in various applications in addition to as the polarizing plate protective film described above. For example, the film of the present disclosure may be favorably employed as an optical compensation film in the liquid crystal display apparatus described above. Note that an optical compensation film refers to an optical material that compensates for phase differences which is generally used in a liquid crystal display device, and is synonymous with a phase difference plate and an optical compensation sheet. The optical compensation film has birefringence, and is employed to remove coloration of a display screen of a liquid crystal display device or to improve the viewing angle characteristics.

The film of the present disclosure may be used as an optical compensation film as is, or may be used as a substrate of an optical compensation film, on which an optically anisotropic layer is provided. The optically anisotropic layer is not limited by the optical performance and driving method of the liquid crystal cell in the liquid crystal display device in which the optical film of the present disclosure is used, and any optical anisotropic layer required as an optical compensation film may be employed in combination with the optical film of the present disclosure. The optically anisotropic layer to be used in combination with the optical film of the present disclosure, may be formed from a composition containing a liquid crystal compound or from a thermoplastic film having birefringence.

EXAMPLES

Hereinafter, the present disclosure will be described in detail based on examples. The materials reagents, amounts of substances amount and the ratios thereof, the operations and the like shown in the following examples may be changed as appropriate as long as such changes do not depart from the spirit of the disclosure. Accordingly, the disclosure is not intended to be limited to the following examples.

Synthesis of Bis Type Alicyclic Cardo Phenolic Compounds

Synthesis Example 1

Synthesis of A-10

Compound (A-10), which is a bis type alicyclic cardo phenolic compound of General Formula I, was synthesized. In the synthesis, a hexestrol was prepared as a bisphenol derivative, after obtaining hydrogenated hexestrol (1) by hydrogenation treatment of hexestrol, the hydrogenated hexestrol (1) was oxygenated to become a diketone and the resulting diketone and o-cresol underwent dehydration condensation. Below, we show the synthesis process as chemical formulae of the products obtained at each step.

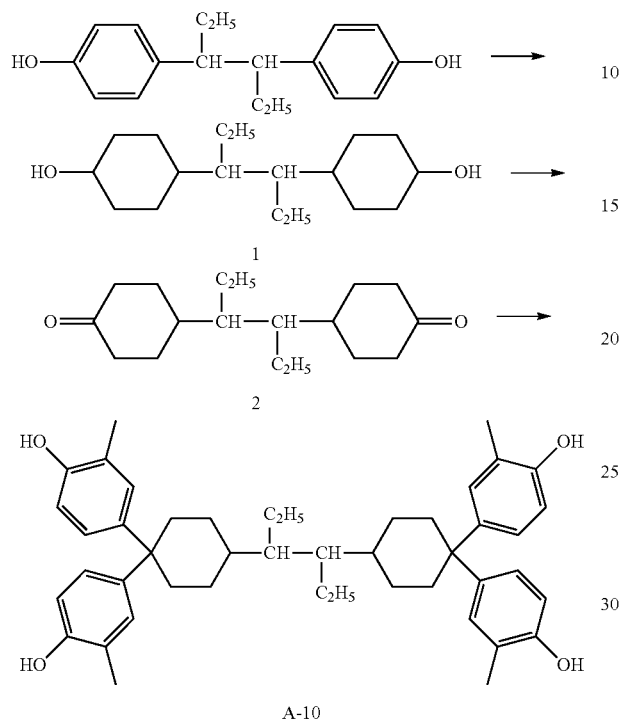

In greater detail, production was performed as follows.

20.0 g of hexestrol, 65 mL of propylene glycol monomethyl ether, and 1.0 g of ruthenium/carbon (wet producing having Ru5% and water 50%) were placed in an 0.5 L autoclave equipped with a thermometer and a stirring blade and the interior of the system was substituted with nitrogen. Then, hydrogen gas was charged up to a pressure of 6.0 MPa, and allowed to react for 6 hours at 165° C. The consumed hydrogen gas was additionally charged, and reactions were caused to occur for another 6 hours at 165° C. It was confirmed that the hydrogen gas was no longer being consumed, and the reaction was terminated. The ruthenium/carbon was removed from the resulting reaction solution by celite filtration, then the reaction solution was concentrated solidified to obtain 20.8 g of hydrogenated hexestrol (1).

20.0 g of the hydrogenated hexestrol (1) and 360 mL of acetone were placed in a 1 L three necked flask equipped with a thermometer, a stirrer, and a reflux tube and cooled with ice. A Jones reagent (10.35 g of $CrO_3$, 9.0 mL of concentrated sulfuric acid, and 45 mL of water), was dropped into the three necked flask and reacted at room temperature for 3 hours. After completion of the reaction, 14 g of sodium hydrogen sulfite was added to remove insoluble matter by decantation, and a liquid separation wash was carried out after 500 mL of ethyl acetate was added. The resulting organic layer was dried with magnesium sulphate, then concentrated and solidified to obtain 19 g of an amorphous solid. 15.9 g of a diketone derivative (2) was obtained by purifying the obtained amorphous solid with a silica gel column (hexane/ethyl acetate=1/1).

10.0 g of the diketone derivative (2), 23.3 g of o-cresol, 0.19 g of mercaptopropionic acid, and 120 mL of toluene were placed in a 500 mL three necked flask equipped with a thermometer, a stirrer, and a reflux pipe. 7.04 g of concentrated sulfuric acid was dropped into the three necked flask under a nitrogen stream and a temperature of 40° C., and reactions were caused to occur for 1 hour at 60° C. After the reactions were completed, 500 mL of ethyl acetate was added to carry out a liquid separation wash. The resulting organic layer was dried with magnesium sulphate, then concentrated and solidified to obtain 30 g of an amorphous solid. 17.9 g of the intended compound A-10 was obtained as a white solid by purifying the amorphous solid with a silica gel column (hexane/ethyl acetate=1/1).

Figure 4:
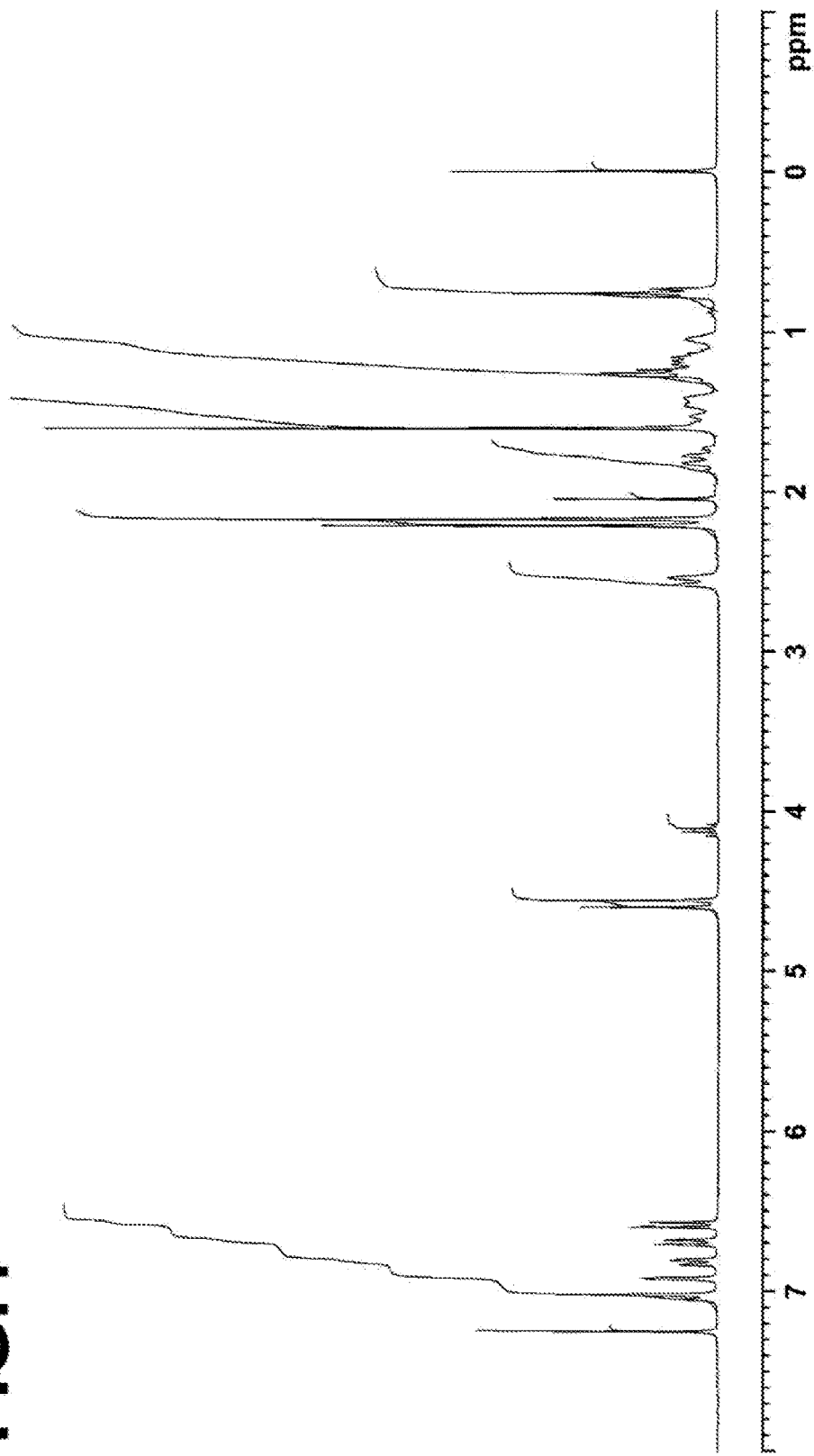
FIG. 4 is a diagram showing a proton NMR (nuclear magnetic resonance spectrum) chart of a bis type alicyclic cardo phenol compound obtained as Synthesis Example 1 in the embodiment.

A proton NMR chart of the obtained bis type alicyclic cardo phenol compound A-10 is illustrated in FIG. 4.

Synthesis Example 2

Synthesis of A-1

Intended compound A-1 (27 g, white crystals) was obtained by the same method as that for Synthesis Example 1, except that the hexestrol bisphenol derivative was changed to 4,4'-biphenol.

Synthesis Example 3

Synthesis of A-2

Intended compound A-2 (32 g, white crystals) was obtained by the same method as that for Synthesis Example 1, except that the hexestrol bisphenol derivative was changed to 2,2-bis(4-hydroxyphenyl) propane.

Synthesis Example 4

Synthesis of A-6

Intended compound A-6 (21 g, light yellow amorphous solid) was obtained by the same method as that for Synthesis Example 1, except that the hexestrol bisphenol derivative was changed to 1,2-bis(4-hydroxyphenyl) ethane.

Synthesis Example 5

Synthesis of A-14

Intended compound A-14 (30 g, light yellow amorphous solid) was obtained by the same method as that for Synthesis Example 1, except that the o-cresol was changed to phenol.

Synthesis Example 6

Synthesis of A-17

Intended compound A-17 (39 g, white crystals) was obtained by the same method as that for Synthesis Example 1, except that the o-cresol was changed to 2-tert-butylphenol.

Synthesis Example 7

Synthesis of A-25

Intended compound A-25 (35 g, white crystals) was obtained by the same method as that for Synthesis Example 1, except that the o-cresol was changed to 2,6-dimethylphenol.

Synthesis Example 8

Synthesis of A-26

Intended compound A-26 (35 g, pale yellow crystals) was obtained by the same method as that for Synthesis Example 1, except that the o-cresol was changed to 2,6-dichlorophenol.

<Preparation of Film>
(Dope Preparation Step: Preparation of Resin Composition)

Dope compositions were prepared by placing 100 parts by mass of the resins shown in Table 1, the parts by mass of the bis type alicyclic cardo compounds shown in Table 1 or compound C-1 and the parts by mass of a brittleness improving agent (Kaneka Corp. Kane Ace M210) shown in Table 1, 534 parts by mass of dichloromethane, and 46 parts by mass of methanol into a mixing tank and stirring while applying heat to dissolve the components.

Resins A through G in Table 1 are as follows. MMA is a structural unit derived from methyl methacrylate, and MA represents a structural unit derived from methyl acrylate.

Resin A: cellulose acetate LT-35, manufactured by Daicel Chemical Industries, Ltd.
Resin B: Arton G7801, JSR Corp.
Resin C: NOVAREX G7022R, Mitsubishi Engineering Plastics Co., Ltd.
Resin D: Purekishiimido TT50, Daicel Evonik Ltd.
Resin E: Delpet 80N, manufactured by Asahi Kasei Chemicals Corporation,
Weight average molecular weight Mw=100,000; Composition ratio of the structural units MMA/MA=95/5 (weight ratio)
Resin F: DIANAL BR85, manufactured by Mitsubishi Rayon Co., Ltd.
Weight average molecular weight Mw=400,000, structural unit MMA100 mass %
Resin G: DIANAL BR88, manufactured by Mitsubishi Rayon Co., Ltd.
Weight average molecular weight MW=1,000,000, structural unit MMA100 mass %

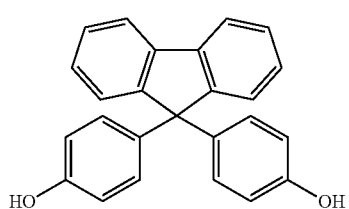

C-1

(Casting Process)

Using the film production line shown in FIG. 3, the prepared resin compositions (dope compositions) were uniformly flow cast from the casting die onto a 2000 mm wide stainless steel casting support to form cast films.

(Peeling Process)

The cast films were peeled off of the casting support at points in time when the amount of residual solvent within the resin compositions became 20 mass %.

The peeled films were conveyed through the tenter without being actively stretched, and dried at 140° C. in a drying zone.

Films having thicknesses of 40 μm were produced by the above processes. Single layers of the films obtained in this manner were designated as polarizing plate protective films of each example.

<Evaluation of Polarizing Plate Protective Film>

The haze, the heat resistance, the moisture permeability, and the brittleness of the obtained polarizing plate protective film were measured by the following methods. The results of measurements are shown in Table 1.

(Haze)

Haze was measured for 40 mm×80 mm film samples cut out from the polarizing plate protective films using haze meter "HGM-2DP" by Suga Test Instruments Co., Ltd., at 25° C. and a relative humidity of 60%, according to JIS K-6714.
A: haze is less than 0.5%.
B: haze is 0.5% or greater and less than 1.0%.
C: haze is 1.0% or greater.

(Heat Resistance)

Heat resistance was measured by measuring glass transition temperatures Tg using a differential scanning calorimeter (6200R) by Seiko Instruments (SII) according to JIS K-7121, and evaluated according to the following criteria.
A: Tg is 115° C. or greater.
B: Tg is 110° C. or greater and less than 115° C.
C: Tg is 105° C. or greater and less than 110° C.

(Moisture Permeability)

The moisture permeabilities (moisture permeabilities as 40 μm converted values) of the films were measured in accordance with the method defined in JIS Z-0208 at a temperature of 40° C. and a relative humidity of 90%, and evaluated according to the following criteria.
A: less than 70 g/m²/day.
B: 70 g/m²/day or greater and less than 80 g/m²/day.
C: 80 g/m²/day or greater and less than 150 g/m²/day.
D: 150 g/m²/day or greater.

(Brittleness)

Brittleness was evaluated by the presence or absence of cracks according to the following criteria.
A: no cracking when folded 10 times by hand (five reciprocal folds)
B: cracking when folded 10 times by hand (five reciprocal folds)
C: cracking when folded 2 times by hand (one reciprocal fold)

TABLE 1

|  | Number | Kane Ace M210 Amount (parts by mass) | Amount (parts by mass) | Resin Number | Evaluation of Film | | | |
|---|---|---|---|---|---|---|---|---|
|  |  |  |  |  | Haze | Heat Resistance | Brittleness | Moisture Permeability (g/m²/day) |
| Example 1 | A-1 | 10 | 12 | E | A | B | B | B |
| Example 2 | A-2 | 10 | 12 | E | A | B | A | B |
| Example 3 | A-6 | 10 | 12 | E | A | B | A | B |

TABLE 1-continued

|  | Kane Number | Amount (parts by mass) | Ace M210 Amount (parts by mass) | Resin Number | Evaluation of Film | | | |
|---|---|---|---|---|---|---|---|---|
|  |  |  |  |  | Haze | Heat Resistance | Brittleness | Moisture Permeability (g/m²/day) |
| Example 4 | A-26 | 10 | 12 | E | A | B | A | B |
| Example 5 | A-25 | 10 | 12 | E | A | B | A | B |
| Example 6 | A-17 | 10 | 12 | E | A | B | A | B |
| Example 7 | A-10 | 10 | 12 | G | A | B | A | B |
| Example 8 | A-14 | 10 | 12 | E | A | B | A | B |
| Example 9 | A-10 | 20 | 12 | G | A | A | B | A |
| Example 10 | A-10 | 20 | 18 | G | A | A | A | A |
| Example 11 | A-17 | 20 | 12 | G | B | A | A | A |
| Example 12 | A-10 | 20 | 0 | A | A | A | A | C |
| Example 13 | A-10 | 20 | 0 | B | A | A | A | C |
| Example 14 | A-10 | 20 | 0 | C | A | A | A | C |
| Example 15 | A-10 | 10 | 12 | D | A | A | A | A |
| Example 16 | A-10 | 10 | 12 | F | A | A | A | A |
| Comparative Example 1 | C-1 | 20 | 12 | E | C | B | B | A |
| Comparative Example 2 | none | 0 | 0 | A | A | A | A | D |
| Comparative Example 3 | none | 0 | 0 | B | A | A | A | D |
| Comparative Example 4 | none | 0 | 0 | C | A | A | A | D |
| Comparative Example 5 | none | 0 | 12 | D | A | A | C | B |
| Comparative Example 6 | none | 0 | 12 | E | A | C | C | B |
| Comparative Example 7 | none | 0 | 12 | F | A | B | C | B |
| Comparative Example 8 | none | 0 | 12 | G | A | A | C | B |

From Table 1 above, it was understood that the polarizing plate protective film of each example has a low haze value, heat resistance greater than or equal to the heat resistance inherent to the resin, and is superior in low moisture permeability.

What is claimed is:

1. A resin composition substantially free of cellulose, comprising:
    an acrylic resin,
    wherein the weight average molecular weight of the acrylic resin is within a range from 250,000 to 2,500,000,
    wherein the acrylic resin includes a unit (a), which is a monomer unit derived from methyl methacrylate, and a unit (b), which is a monomer unit derived from an alkyl (meth) acrylate other than methyl methacrylate, and
    wherein the content of the unit (a) is 95% by mass or greater based on the total weight of the acrylic resin; and
    a compound represented by General Formula I below:

[General Formula I]

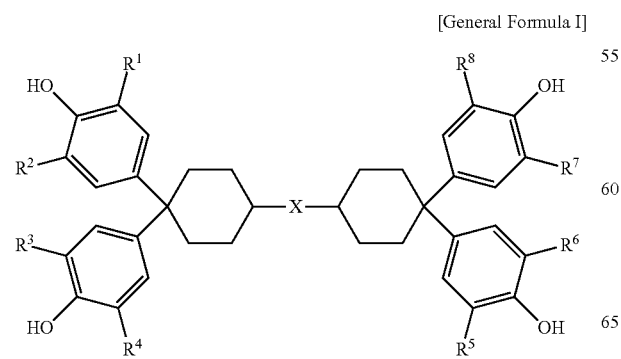

wherein each of $R^1$, $R^2$, $R^3$, $R^4$, $R^5$, $R^6$, $R^7$ and $R^8$ represents a hydrogen atom, a halogen atom, a hydroxyl group, or an aliphatic hydrocarbon group having a carbon number within a range from 1 to 8, and X represents a divalent linking group constituted by at least one species selected from among a single bond, an ether bond, and an alkylene group having a carbon number within a range from 1 to 15.

2. The resin composition as defined in claim 1, wherein:
    X is a divalent group constituted by at least one species selected from among an ether bond and an alkylene group having a carbon number within a range from 1 to 10.

3. The resin composition as defined in claim 1, wherein:
    X is a divalent group constituted by at least one species selected from among an ether bond and an alkylene group having a carbon number within a range from 1 to 10; and
    the number of atoms that bind cyclohexyl groups to each other is at least 2 or greater.

4. The resin composition as defined in claim 1, wherein:
    X is a divalent linking group which is an alkylene group having a carbon number within a range from 4 to 8.

5. The resin composition as defined in claim 1, wherein:
    $R^1$, $R^2$, $R^3$, $R^4$, $R^5$, $R^6$, $R^7$ and $R^8$ are hydrogen atoms or aliphatic hydrocarbon groups having a carbon number within a range from 1 to 8.

6. The resin composition as defined in claim 1, wherein:
    $R^2$, $R^3$, $R^6$, and $R^7$ are hydrogen atoms.

7. The resin composition as defined in claim 1, wherein:
    $R^1$, $R^4$, $R^5$, and $R^8$ are hydrogen atoms or methyl groups.

8. The resin composition as defined in claim 1, wherein:
    the weight average molecular weight of the acrylic resin is within a range from 250,000 to 2,000,000.

9. A film formed by employing the resin composition as defined in claim 1.

10. A polarizing plate protective film comprising at least one layer of the film defined in claim 9.

11. A polarizing plate, comprising:
a polarizer; and
the polarizing plate protective film as defined in claim 10 provided on at least one surface of the polarizer.

12. A liquid crystal display device, comprising:
a pair of polarizing plates; and
a liquid cell sandwiched between the pair of polarizing plates;
at least one of the polarizing plates being the polarizing plate as defined in claim 11.

* * * * *